(12) United States Patent
Chae et al.

(10) Patent No.: US 10,640,527 B2
(45) Date of Patent: May 5, 2020

(54) MESITYLENE-CORED AMPHIPHILES AND USES THEREOF

(71) Applicant: Industry-University Cooperation Foundation Hanyang University Erica Campus, Ansan-si (KR)

(72) Inventors: Pil Seok Chae, Ansan-si (KR); Kyung Ho Cho, Seoul (KR)

(73) Assignee: Industry-University Cooperation Foundation Hanyang University Erica Campus, Anan-si (KR)

(*) Notice: Subject to any disclaimer, the term of this patent is extended or adjusted under 35 U.S.C. 154(b) by 0 days.

(21) Appl. No.: 16/316,622

(22) PCT Filed: Aug. 31, 2016

(86) PCT No.: PCT/KR2016/009716
§ 371 (c)(1),
(2) Date: Jan. 10, 2019

(87) PCT Pub. No.: WO2018/012669
PCT Pub. Date: Jan. 18, 2018

(65) Prior Publication Data
US 2019/0241597 A1 Aug. 8, 2019

(30) Foreign Application Priority Data

Jul. 11, 2016 (KR) .................. 10-2016-0087544

(51) Int. Cl.
| | | |
|---|---|---|
| C07H 15/18 | (2006.01) | |
| C07K 1/14 | (2006.01) | |
| C07K 14/705 | (2006.01) | |
| C07K 14/72 | (2006.01) | |

(52) U.S. Cl.
CPC ............ *C07H 15/18* (2013.01); *C07K 1/145* (2013.01); *C07K 14/705* (2013.01); *C07K 14/723* (2013.01)

(58) Field of Classification Search
None
See application file for complete search history.

(56) References Cited

PUBLICATIONS

International Search Report and the Written Opinion dated Apr. 10, 2017 From the International Seaching Authority Re. Application No. PCT/KR2016/009716. (9 Pages).
Alexander et al. "Sterically Crowded Hexaalkyl Benzne-1,2,3,4,5,6-Hexakis-[Beta-(Alkoxycarbonyl)Propanoates]. Synthesis and Conformation Analysis", Collection of Czechoslovak Chemical Communications, 65(5): 673-694, 2000. p. 674, Scheme 2.
Cong et al. "Synthesis, Structures and Self-Assemblies of Tripodal Malonate, Beta-Diketones and Pyrazolyls Derivatives", Chemical Journal of Chinese Universities, 32(9): 2145-2151, Sep. 2011. English Abstract. p. 2148, Scheme 1.
Dauvergne et al. "Tripod Facial Surfactants With Benzene as the Central Core: Design, Synthesis and Self-Assembly Study", New Journal of Chemistry, 36(5): 1170-1179, Published Online Mar. 1, 2012. p. 1172, Cheme 2.
Dondoni et al. "Synthesis of All Carbon Linked Glycoside Clusters Round Benzene Scaffold Via Sonogashira-Heck-Cassar Cross-Coupling of Iodobenzenes With Ethynyl C-Glycosides", Synlett, 2002(11): 1850-1854, Published Online Oct. 29, 2002. p. 1851, Cheme 3.
Newkome et al. "Cascade Molecules: Synthesis and Characterization of A Benzene[9]3-Arborol", Journal of the American Chemical Society, 108(4): 849-850, 1986. p. 850, Scheme 1.
Newstead et al. "Insights Into Outer Membrane Protein Crystallization", Molecular Membrane Biology, 25(8): 631-638, Dec. 2008.
Newstead et al. "Rationalizing Alpha-Helical Membrane Protein Crystallization", Protein Science, 17(3): 466-472, Mar. 2008.

*Primary Examiner* — Traviss C McIntosh, III

(57) ABSTRACT

The present invention relates to a mesitylene-cored amphiphile, a method of preparing the same and a method of extraction, solubilization, stabilization, crystallization or analysis of a membrane protein using the same. When a mesitylene-cored compound according to the present invention is used, membrane proteins can be stored in a stable conformation for a long time in an aqueous solution in comparison with conventional compounds, by which the membrane proteins are usable in both functional and structural analyses thereof. The functional and structural analyses of membrane proteins are one of the fields that are most spotlighted in current biology and chemistry. The present invention can be used to research on a protein structure closely related to new drug development.

14 Claims, 25 Drawing Sheets

MGA-C10 : R = n-C₄H₉
MGA-C11 : R = n-C₅H₁₁
MGA-C12 : R = n-C₆H₁₃
MGA-C13 : R = n-C₇H₁₅
MGA-C14 : R = n-C₈H₁₇
MGA-C15 : R = n-C₉H₁₉

MGA-C10

XMA-C8 : R = n-C₄H₉
XMA-C9 : R = n-C₅H₁₁
XMA-C10 : R = n-C₆H₁₃
XMA-C11 : R = n-C₇H₁₅
XMA-C12 : R = n-C₈H₁₇

XGA-C4 : R = n-C₂H₅
XGA-C5 : R = n-C₃H₇
XGA-C6 : R = n-C₄H₉
XGA-C7 : R = n-C₅H₁₁

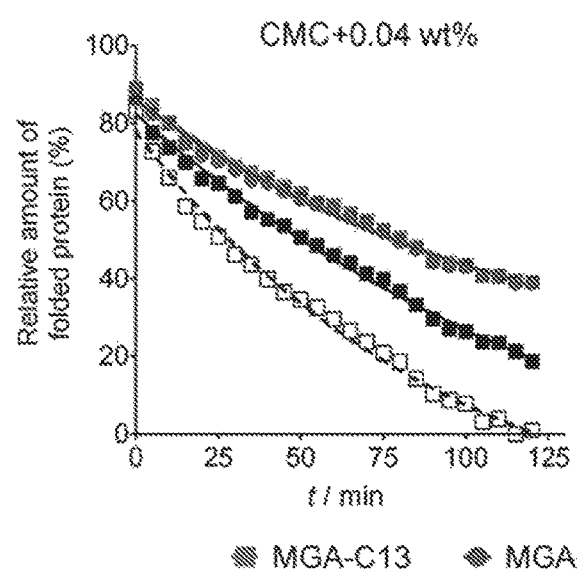
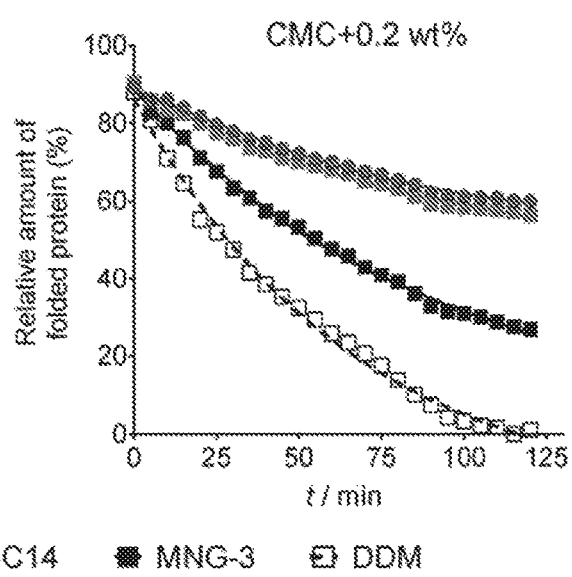
Figure 25(a)
Figure 25(b)

MESITYLENE-CORED AMPHIPHILES AND USES THEREOF

RELATED APPLICATIONS

This application is a National Phase of PCT Patent Application No. PCT/KR2016/009716 having International filing date of Aug. 31, 2016, which claims the benefit of priority of Korean Patent Application No. 10-2016-0087544 filed on Jul. 11, 2016. The contents of the above applications are all incorporated by reference as if fully set forth herein in their entirety.

FIELD AND BACKGROUND OF THE INVENTION

The present invention relates to a newly developed mesitylene-cored amphiphile and a method of extraction, solubilization, stabilization, crystallization or analysis of a membrane protein using the same.

Membrane proteins play an important role in biological systems. Since these bio-macromolecules contain hydrophilic and hydrophobic portions, amphiphilic molecules are required for extraction of membrane proteins from cell membranes, and solubilization and stabilization of membrane proteins in an aqueous solution.

Membrane protein crystals with high quality have to be obtained for structural analysis of membrane proteins. To this end, the securement of the structural stability of membrane proteins in an aqueous solution has to come first. The number of conventional amphiphilic molecules that have been used in membrane protein research is 100 or more, while only five of them have been actively utilized in membrane protein structure research. These five amphiphilic molecules include n-octyl-β-D-glucopyranoside (OG), n-nonyl-β-D-glucopyranoside (NG), n-decyl-β-D-maltopyranoside (DM), n-dodecyl-β-D-maltopyranoside (DDM), and lauryldimethylamine-N-oxide (LDAO) (see Non-Patent Documents 1 and 2). However, since membrane proteins surrounded by these molecules easily denature or aggregate to cause loss of function, research for the function and structure of membrane proteins using these molecules has significant limitations. This is because conventional molecules have a simple chemical structure that fails to show a diversity of characteristics. Accordingly, there is a need for the development of novel amphiphiles with a new structure and excellent properties.

Thus, the inventors developed novel amphiphiles that can be used in membrane protein research, thereby reaching the present invention.

SUMMARY OF THE INVENTION

An object of the present invention is to provide a compound represented by the following Formula 1.

Another object of the present invention is to provide a composition for extraction, solubilization, stabilization, crystallization or analysis of a membrane protein including the compound.

Yet another object of the present invention is to provide a method of preparing the compound.

Still another object of the present invention is to provide a method of extraction, solubilization, stabilization, crystallization or analysis of a membrane protein using the compound.

An embodiment of the present invention provides a compound represented by the following Formula 1:

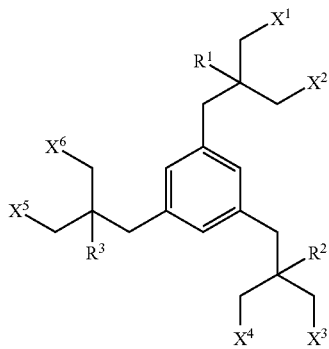

[Formula 1]

In Formula 1, $R^1$, $R^2$ and $R^3$ each may independently represent a substituted or unsubstituted C3 to C30 alkyl group, a substituted or unsubstituted C3 to C30 cycloalkyl group, or a substituted or unsubstituted C3 to C30 aryl group; and $X^1$, $X^2$, $X^3$, $X^4$, $X^5$ and $X^6$ each may independently represent an oxygen-linked saccharide.

The term "saccharide" as used herein refers to a compound which has a relatively small molecule size among carbohydrates and tastes sweet when dissolved in water. Saccharides are classified as monosaccharides, disaccharides and polysaccharides according to the number of monomer molecules forming saccharides.

The saccharide used in the embodiment of the present invention may be a monosaccharide or a disaccharide, specifically, may be glucose or maltose, but is not limited thereto.

The saccharide may serve as a hydrophilic group. The compound according to an embodiment of the present invention allows a protein-detergent complex (PDC) with a small size formed of the compound and a membrane protein by connecting six saccharides, which are hydrophilic groups, in parallel for increasing a size of the hydrophilic group while minimizing an increase in the length. When a complex formed of the compound and the membrane protein has a small size, membrane protein crystals with high quality can be obtained (G. G. Prive, Methods 2007, 41, 388-397).

Furthermore, $R^1$, $R^2$ and $R^3$ may function as a hydrophobic group. The compound according to an embodiment of the present invention has three hydrophobic groups introduced for the optimum hydrophile-lipophile balance.

The compound according to an embodiment of the present invention may have a mesitylene linker that is structurally rigid. That is, since the flexibility of a whole molecule is highly restricted by introducing three quaternary carbons to terminal ends of mesitylene, crystallization of a membrane protein can be promoted.

Specifically, $R^1$ to $R^3$ may represent a substituted or unsubstituted $C_3$ to $C_{30}$ alkyl group; and $X^1$ to $X^6$ may represent an oxygen-linked glucose. In an embodiment of the present invention, these compounds are referred to as "mesitylene-cored glucoside amphiphiles (MGAs)".

In an embodiment of the present invention, a compound in which $R^1$ to $R^3$ represent a $C_{10}$ alkyl group; and $X^1$ to $X^6$ represent an oxygen-linked glucose, is referred to as "MGA-C10". Accordingly, the compound may be a compound represented by the following Formula 2:

[Formula 2]

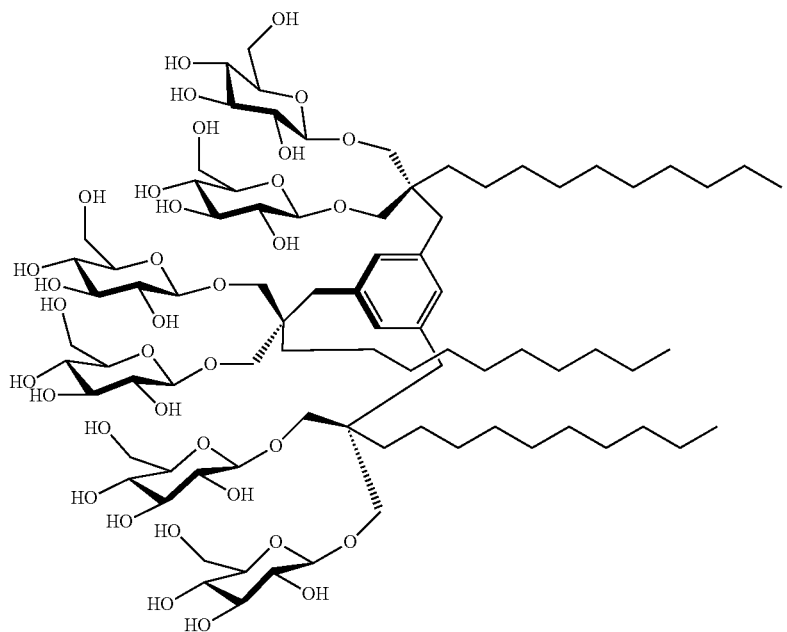

In an embodiment of the present invention, a compound in which $R^1$ to $R^3$ represent a $C_{11}$ alkyl group; and $X^1$ to $X^6$ represent an oxygen-linked glucose, is referred to as "MGA-C11". Therefore, the compound may be a compound represented by the following Formula 3:

[Formula 3]

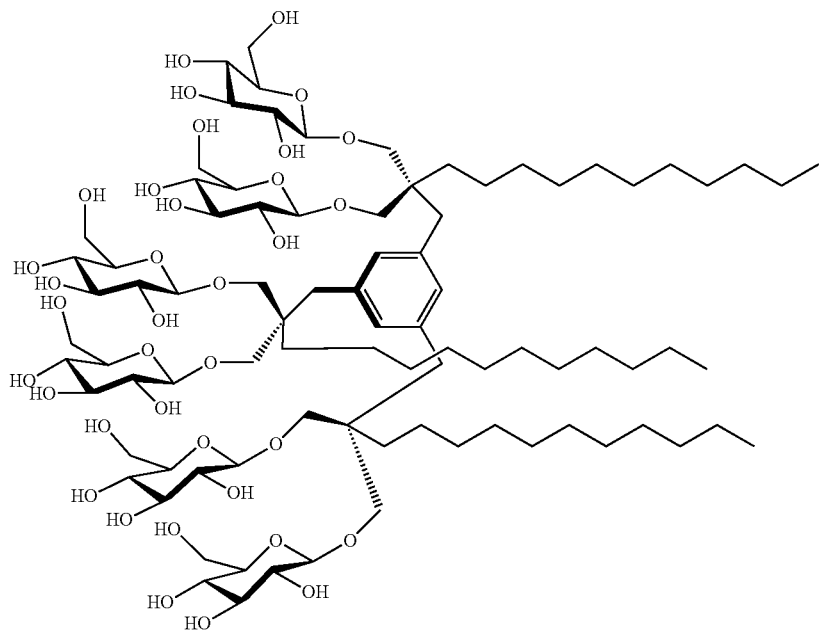

In an embodiment of the present invention, a compound in which $R^1$ to $R^3$ represent a $C_{12}$ alkyl group; and $X^1$ to $X^6$ represent an oxygen-linked glucose, is referred to as "MGA-C12". Consequently, the compound may be a compound represented by the following Formula 4:

[Formula 4]

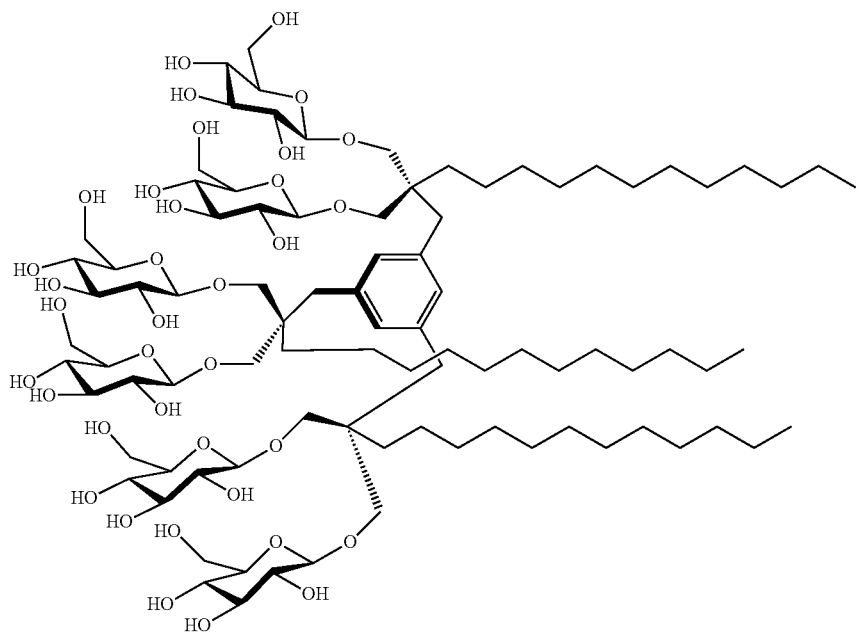

In an embodiment of the present invention, a compound in which $R^1$ to $R^3$ represent a $C_{13}$ alkyl group; and $X^1$ to $X^6$ represent an oxygen-linked glucose, is referred to as "MGA-C13". Thus, the compound may be a compound represented by the following Formula 5:

[Formula 5]

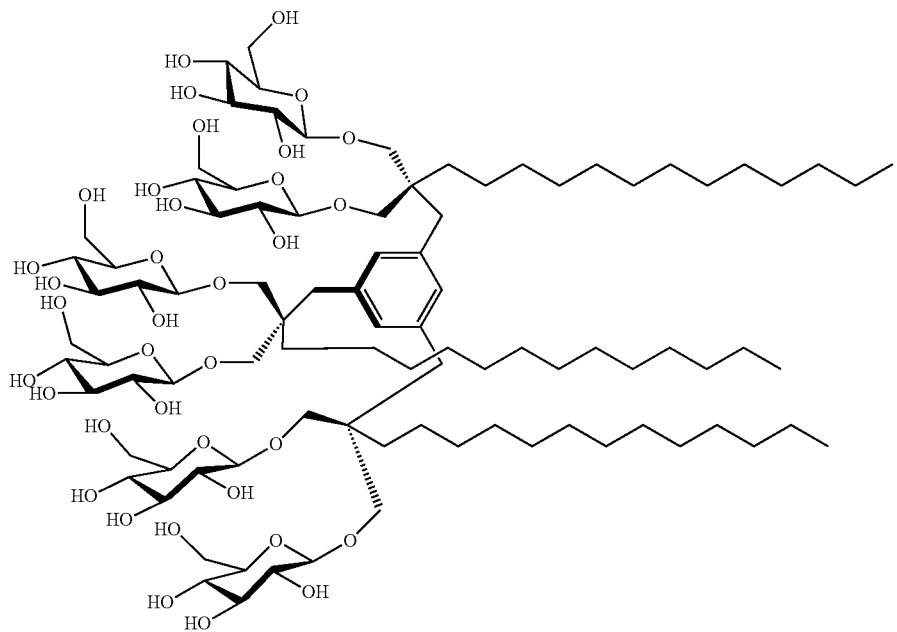

In an embodiment of the present invention, a compound in which $R^1$ to $R^3$ represent a $C_{14}$ alkyl group; and $X^1$ to $X^6$ represent an oxygen-linked glucose, is referred to as "MGA-C14". Thus, the compound may be a compound represented by the following Formula 6:

[Formula 6]

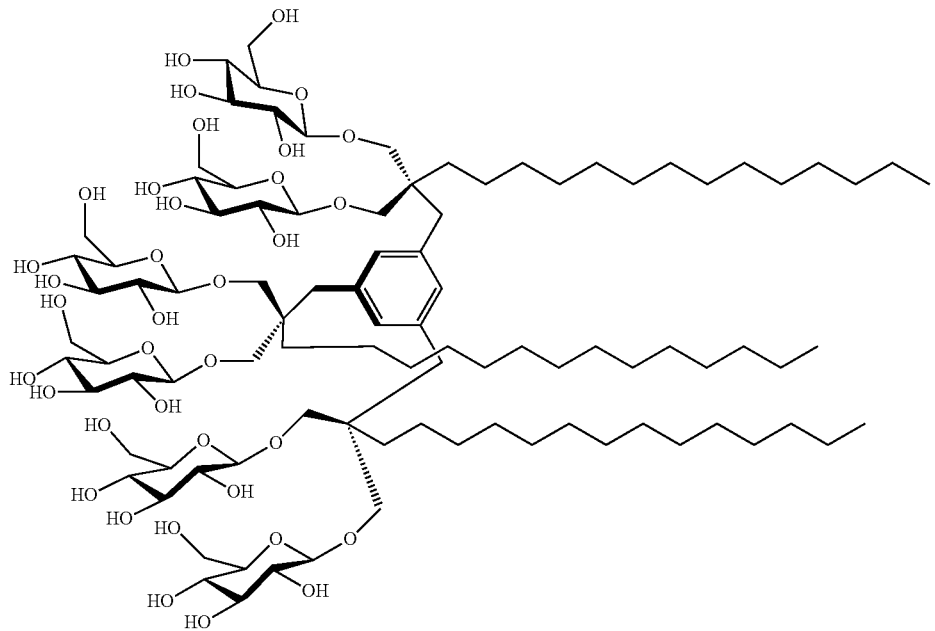

In an embodiment of the present invention, a compound in which $R^1$ to $R^3$ represent a $C_{15}$ alkyl group; and $X^1$ to $X^6$ represent an oxygen-linked glucose, is referred to as "MGA-C15". Thus, the compound may be a compound represented by the following Formula 7:

[Formula 7]

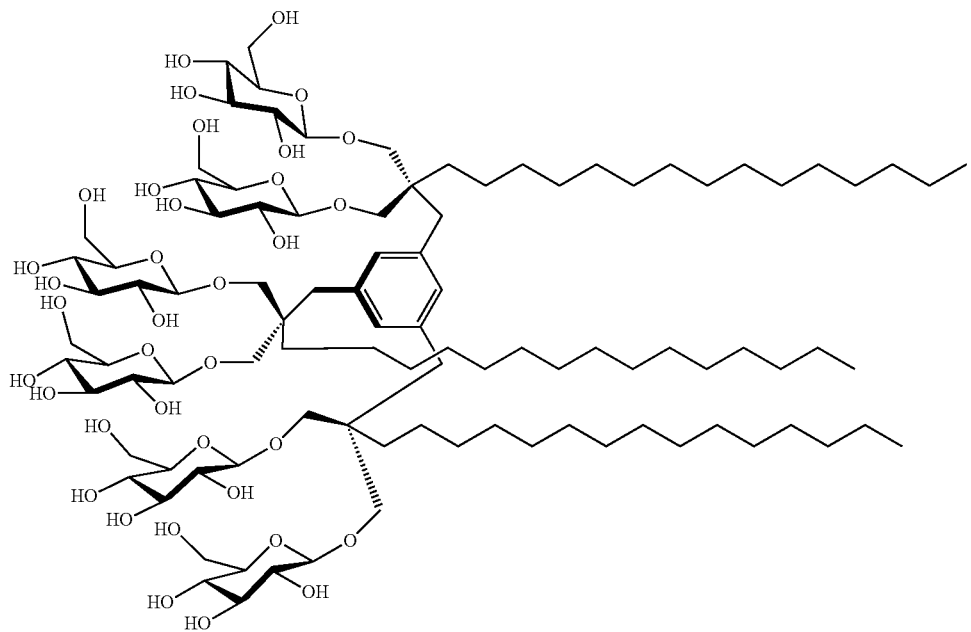

A compound according to another embodiment of the present invention may be an amphiphilic molecule for extraction, solubilization, stabilization, crystallization or analysis of a membrane protein, but is not limited thereto.

Specifically, the extraction may be extraction of a membrane protein from the cell membrane.

The term "amphiphilic molecule" as used herein refers to a molecule which possesses both a hydrophobic group and a hydrophilic group to have affinity for both polar and nonpolar solvents. Surfactants and phospholipid molecules existing in cell membranes have a hydrophilic group at one end and a hydrophobic group at another end to possess amphiphilic properties, and are characterized by forming micelles or liposomes in an aqueous solution. While hydrophilic groups are polar groups, amphiphilic molecules tend to be insoluble in water due to the coexistence of non-polar groups. However, when a concentration reaches a certain critical micelle concentration (CMC) or higher, a micelle in which hydrophobic groups gather inward by a hydrophobic interaction and hydrophilic groups are exposed at a surface is formed, such that water-solubility increases.

A method of measuring a CMC is not particularly limited, and those methods widely known in the related field may be used. For example, a CMC may be measured by a fluorophore encapsulation method using diphenylhexatriene (DPH).

A compound according to an embodiment of the present invention may have a CMC in a range of 0.1 to 10,000 μM in an aqueous solution, specifically 0.1 to 1,000 μM, more specifically 0.1 to 100 μM, still more specifically 0.1 to 50 μM, even more specifically 0.1 to 20 μM, even more specifically 0.5 to 20 μM, for example, 1.0 to 10 μM, but is not limited thereto.

While DDM mainly used in conventional membrane protein research has a CMC of 170 μM, the CMC values of MGAs according to the present embodiment are very low. Therefore, it can be determined that MGAs are more excellent than DDM in that micelles can be easily formed with only a small amount of MGAs such that MGAs enable effective research and analysis of membrane proteins.

Furthermore, still another embodiment of the present invention provides a composition for extraction, solubilization, stabilization, crystallization or analysis of a membrane protein including the compound.

Specifically, the extraction may be extraction of a membrane protein from a cell membrane.

The composition may be in a micelle, liposome, emulsion or nanoparticle form, but is not limited thereto.

The micelle may have a radius between 2.0 to 20 nm, specifically 2.0 to 5.0 nm, more specifically 2.3 to 4.3 nm, still more specifically 2.5 to 4.0 nm, for example, 2.8 to 3.7 nm, but is not limited thereto.

A method of measuring a radius of the micelle is not particularly limited, and those methods widely known in the related field may be used, for example, a dynamic light scattering (DLS) experiment may be used for measurement.

As compared to DDM with a radius of 3.4 nm, MGAs according to the present embodiment have a similar micelle size, and thus it can be found that these novel molecules have a similar geometric shape as DDM in an aqueous solution.

The micelles, liposomes, emulsions or nanoparticles may interact with membrane proteins through hydrophobic interaction. In other words, the micelle, liposomes, emulsions or nanoparticles may extract membrane proteins existing in cell membranes and envelop the membrane proteins. Thus, the micelle allows extraction, solubilization, stabilization, crystallization or analysis of membrane proteins from cell membranes.

The composition may further include a buffer or the like that may be helpful in extraction, solubilization, stabilization, crystallization or analysis of a membrane protein.

Moreover, yet another embodiment of the present invention provides a method of preparing a compound represented by the following Formula 1, including the steps of:

1) performing a monoalkylation reaction on diethyl malonate to introduce an alkyl group;

2) reacting the product prepared in step 1) with 1,3,5-tris(bromomethyl)benzene to introduce a mesitylene linker;

3) reducing an ester group of the product prepared in step 2) to an alcohol group;

4) performing a glycosylation reaction on the product prepared in step 3) to introduce a saccharide with a protecting group; and 5) performing a deprotection reaction on the product prepared in step 4):

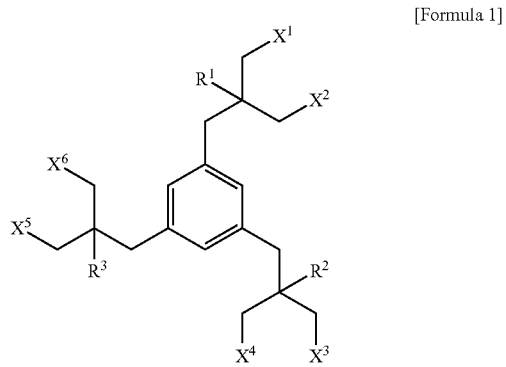

[Formula 1]

In Formula 1, $R^1$, $R^2$ and $R^3$ each independently represent a substituted or unsubstituted C3 to C30 alkyl group, a substituted or unsubstituted C3 to C30 cycloalkyl group, or a substituted or unsubstituted C3 to C30 aryl group; and $X^1$, $X^2$, $X^3$, $X^4$, $X^5$ and $X^6$ each independently represent an oxygen-linked saccharide.

Specifically, $R^1$ to $R^3$ may represent a substituted or unsubstituted $C_3$ to $C_{30}$ alkyl group; and $X^1$ to $X^6$ may represent an oxygen-linked glucose.

The compound may be a compound represented by Formulas 2 to 7 according to an embodiment of the present invention, but is not limited thereto.

In the present embodiment, a compound can be synthesized from readily available diethyl malonate using a simple method. As such, since the preparation method according to the present invention allows easy synthesis of a compound, mass production of the compound for membrane protein research can be realized.

In an embodiment of the present invention, MGAs are prepared by performing the following steps in accordance with a synthesis scheme as illustrated in FIG. 1:

1) 1-bromoalkane and $K_2CO_3$ are added to diethyl malonate dissolved in THF and DMF to perform a monoalkylation reaction, thereby obtaining compound A;

2) 1,3,5-tris(bromomethyl)benzene and NaH are added to compound A dissolved in THF and DMF, thereby obtaining product B to which a mesitylene linker is introduced;

3) $LiAlH_4$ and THF are added to product B to reduce an ester group to an alcohol group, thereby obtaining product C;

4) A perbenzoylated glucosylbromide, AgOTf and $CH_2Cl_2$ are added to product C to perform a glycosylation reaction, thereby obtaining product D to which a saccharide with a protecting group is introduced; and 5) NaOMe and MeOH are added to product D and a deprotection reaction (de-O-benzoylation) is carried out to obtain product E (MGAs).

Further, yet another embodiment of the present invention provides a method of extraction, solubilization, stabilization, crystallization or analysis of a membrane protein, specifically, provides a method of extraction, solubilization, stabilization, crystallization or analysis of a membrane protein which includes a step of treating a membrane protein with a compound represented by the following Formula 1 in an aqueous solution:

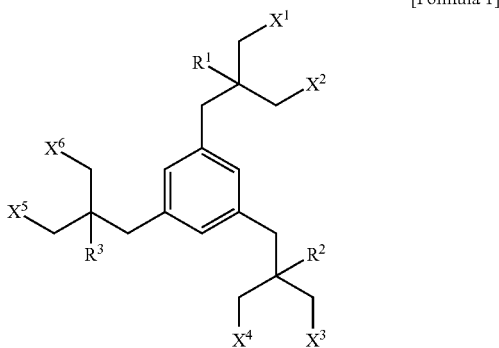

[Formula 1]

In Formula 1, $R^1$, $R^2$ and $R^3$ each independently represent a substituted or unsubstituted C3 to C30 alkyl group, a substituted or unsubstituted C3 to C30 cycloalkyl group, or a substituted or unsubstituted C3 to C30 aryl group; and $X^1$, $X^2$, $X^3$, $X^4$, $X^5$ and $X^6$ each independently represent an oxygen-linked saccharide.

Specifically, $R^1$ to $R^3$ may represent a substituted or unsubstituted $C_3$ to $C_{30}$ alkyl group; and $X^1$ to $X^6$ may represent an oxygen-linked glucose.

The compound may be a compound represented by Formulas 2 to 7 according to an embodiment of the present invention, but is not limited thereto.

Specifically, the extraction may be extraction of a membrane protein from a cell membrane.

The term "membrane protein" as used herein is a generic term for proteins or glycoproteins present in cell membranes. These membrane proteins exist in various states such as passing through the entire membrane layer, being positioned at a surface layer or being grafted to a side of a cell membrane, etc. Examples of membrane proteins include receptors such as enzymes, peptide hormones, local hormones and the like, acceptable carriers such as saccharides and the like, ion channels, cell membrane antigens, etc., but are not limited thereto.

The membrane proteins include any proteins or glycoproteins present in cell membranes, and specifically may be selected from a group comprising of uric acid-xanthine/$H^+$ symporter (UapA), melibiose permease (MelB), leucine transporter (LeuT), human $\beta_2$ adrenergic receptor ($\beta_2$AR), and combinations thereof, but is not limited thereto.

The term "extraction of membrane proteins" as used herein refers to separating membrane proteins from cell membranes.

The term "solubilization of membrane proteins" as used herein refers to dissolving membrane proteins, which are insoluble in water, in micelles in an aqueous solution.

The term "stabilization of membrane proteins" as used herein refers to stably preserving a tertiary or quaternary structure such that the structure and function of membrane proteins are not changed.

The term "crystallization of membrane proteins" as used herein refers to forming crystals of membrane proteins in a solution.

The term "analysis of membrane proteins" as used herein refers to analyzing the structure or function of membrane proteins. In an embodiment, analysis of membrane proteins may be carried out using a known method, and for example, analysis of the structure of membrane proteins may be conducted by electron microscopy or nuclear magnetic resonance, without being limited thereto.

BRIEF DESCRIPTION OF THE SEVERAL VIEWS OF THE DRAWINGS

The above and other objects, features and advantages of the present invention will become more apparent to those of ordinary skill in the art by describing in detail exemplary embodiments thereof with reference to the accompanying drawings, in which.

20(a) a concentration of MGAs or DDM is CMC+0.04 wt %; and

Figure 21A:
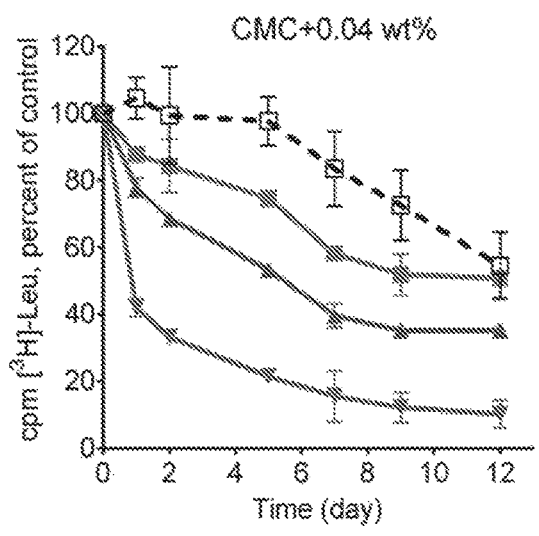
Figure 21B:
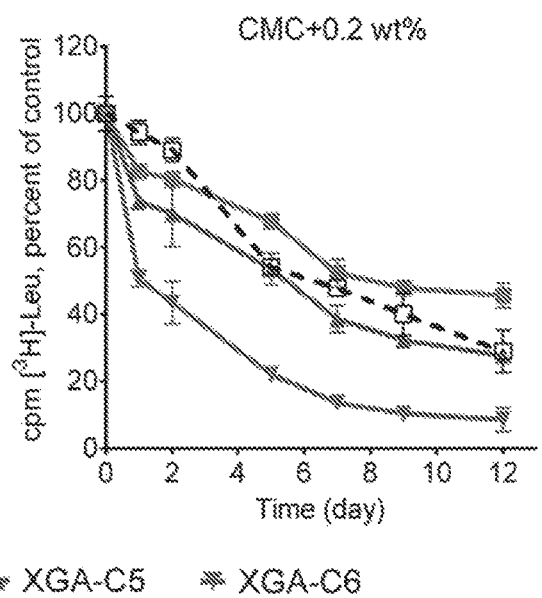

20(b) a concentration of MGAs or DDM is CMC+0.2 wt %;

FIGS. 21(a) and 21(b) illustrate a result of measuring the structural stability of LeuTsolubilized in XGAs (XGA-C4, XGA-C5 and XGA-C6) or DDM in an aqueous solution. Protein stability was determined by measuring a ligand-binding activity of receptors using SPA. The ligand-binding activity of the transporter was measured at regular intervals while LeuT was incubated at room temperature for 12 days in the presence of each amphiphile:

21(a) a concentration of XGAs or DDM is CMC+0.04 wt %; and

Figure 22:
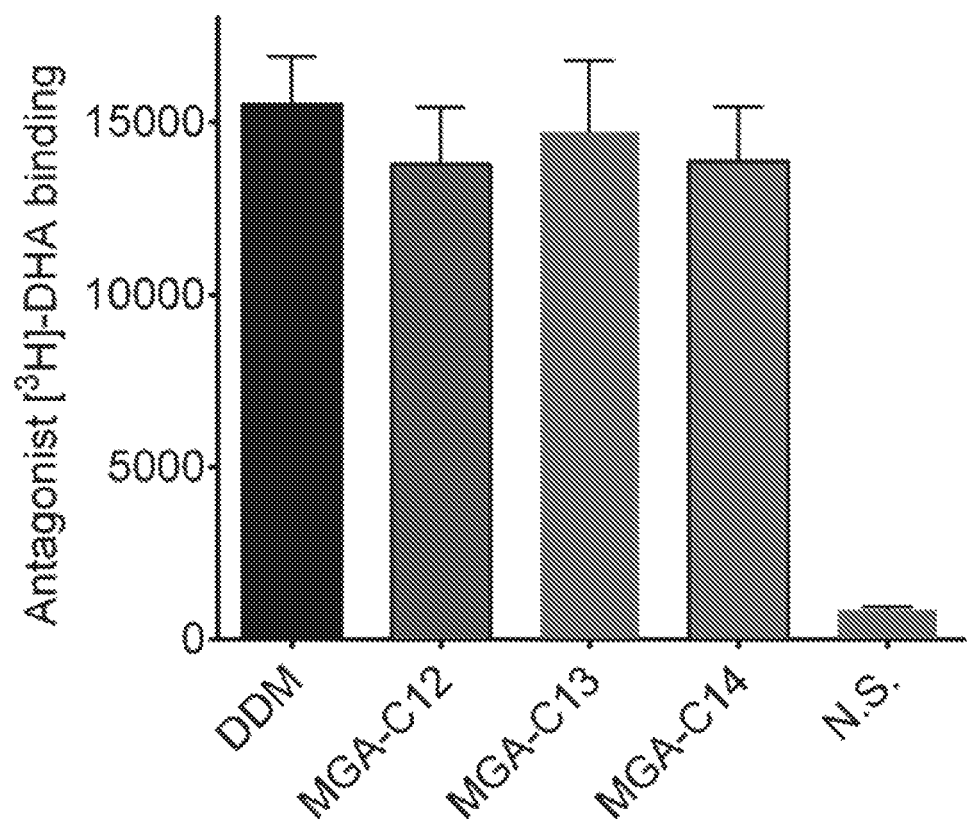
Figure 23:
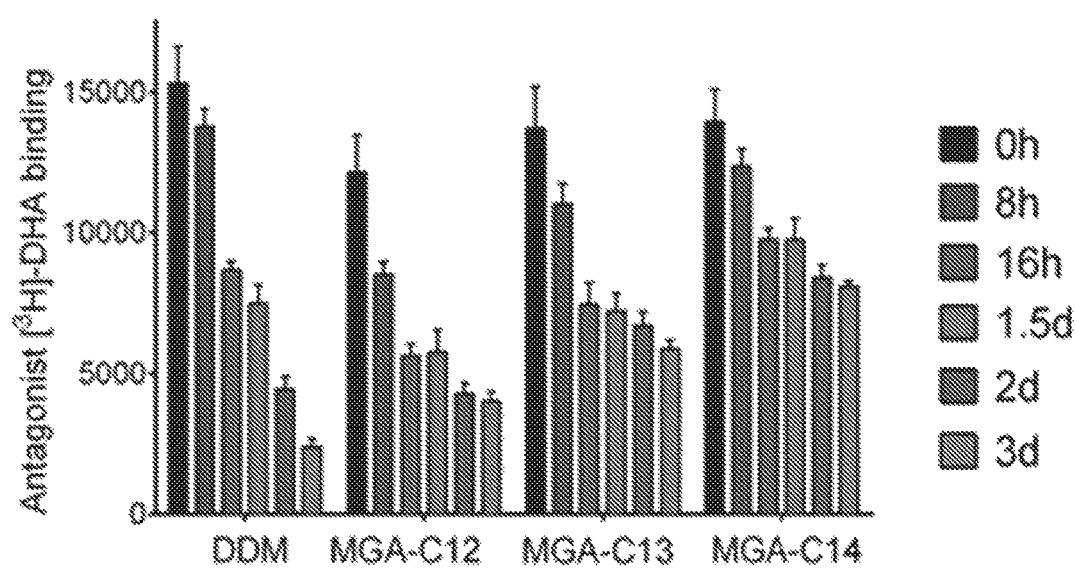
Figure 24A:
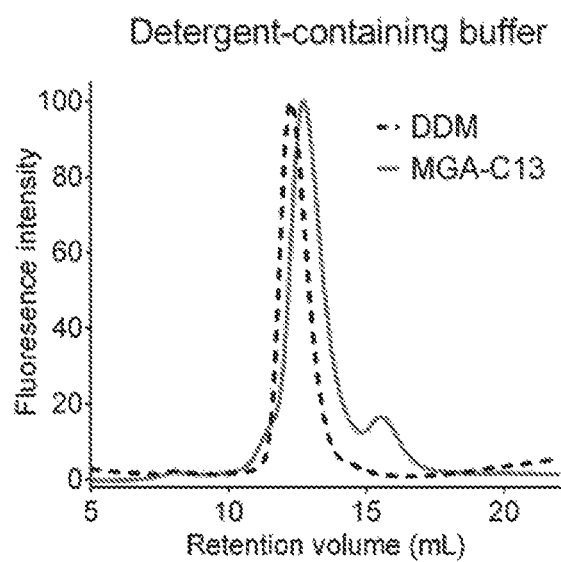
Figure 24B:
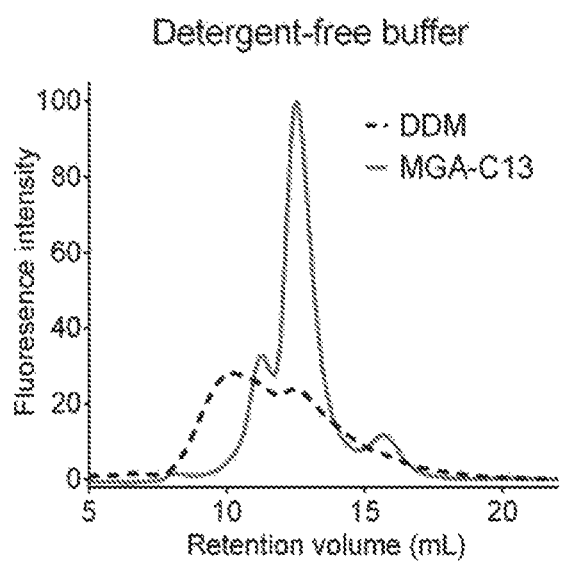

21(b) a concentration of XGAs or DDM is CMC+0.2 wt %;

FIG. 22 illustrates a result of measuring a ligand ([$^3$H]-DHA) binding activity of $\beta_2$AR dissolved in MGAs (MGA-C12, MGA-C13, MGA-C14) or DDM;

FIG. 23 illustrates a result of measuring the structural stability of $\beta_2$AR solubilized in MGAs (MGA-C12, MGA-C13, and MGA-C14) or DDM. Protein stability was determined by measuring a ligand-binding activity of the receptor. The ligand-binding activity of the receptor was measured at regular intervals (0 hours, 8 hours, 16 hours, 1.5 days, 2 days and 3 days) while $\beta_2$AR was incubated at room temperature for three days in the presence of each amphiphile;

FIGS. 24(a) and 24(b) illustrate a size exclusion chromatography (SEC) profile of $\beta_2$AR solubilized by DDM or MGA-C13 in an (a) amphiphiles-containing buffer or an (b) amphiphile-free buffer; and FIGS. 25(a) and 25(b) illustrate a result of measuring the thermal stability of UapA solubilized in MGAs (MGA-C13, MGA-C14), MNG-3 or DDM in an aqueous solution. A relative amount of folded proteins was measured using a CPM assay:

25(a) a concentration of MGAs (MGA-C13, MGA-C14), MNG-3 or DDM is CMC+0.04 wt %; and 25(b) a concentration of MGAs (MGA-C13, MGA-C14), MNG-3 or DDM is CMC+0.2 wt %.

DESCRIPTION OF SPECIFIC EMBODIMENTS OF THE INVENTION

Hereinafter, the present invention will be described in detail with reference to the following examples. The present invention may be embodied in many different forms without departing from the spirit and significant characteristics of the invention. Therefore, the embodiments of the present invention are disclosed only for illustrative purposes and should not be construed as limiting the present invention.

<Example 1> Synthetic Method of MGAs

Figure 1:
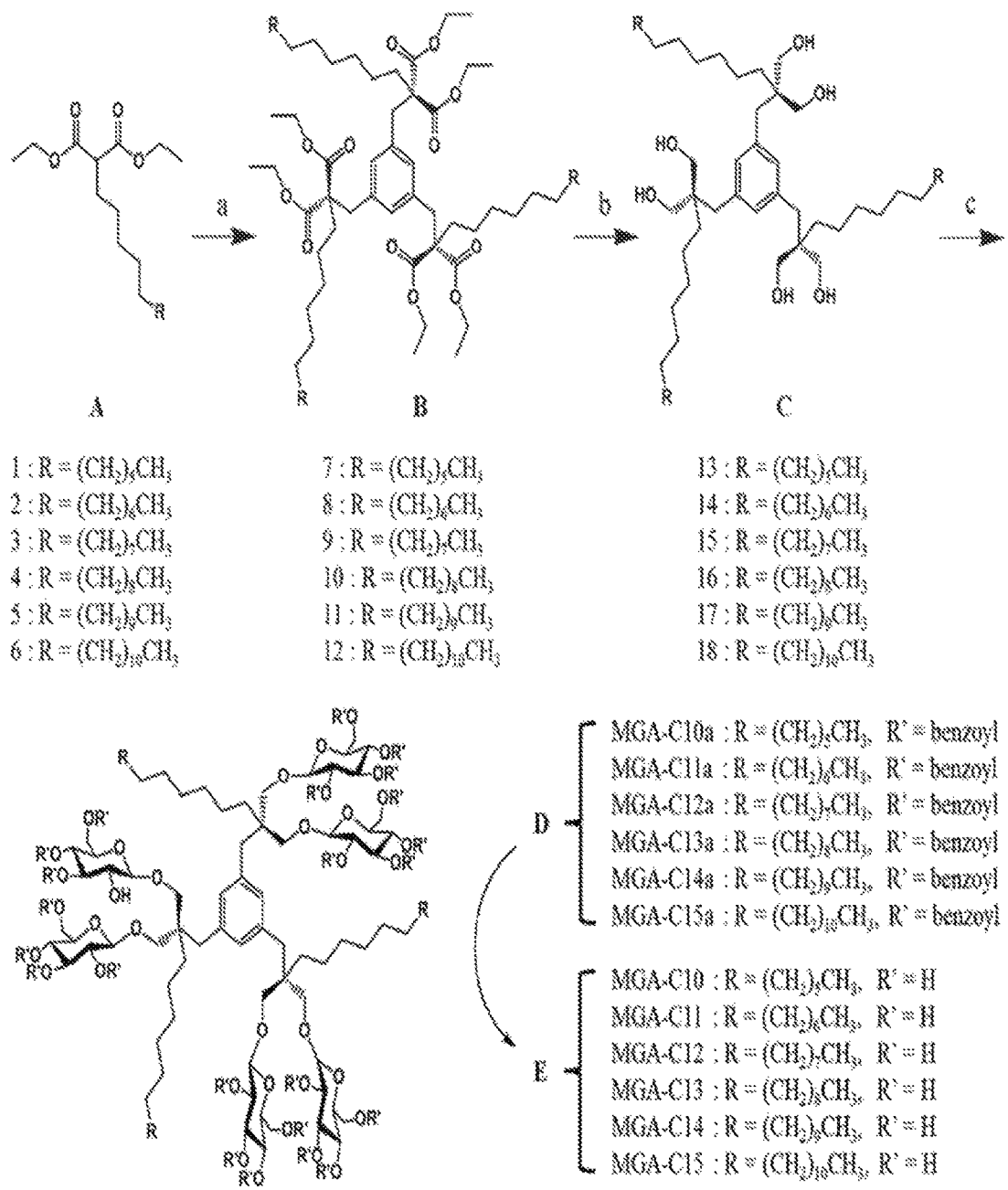
FIG. 1 illustrates a synthesis scheme of MGAs according to Example 1 of the present invention.
Figure 2:
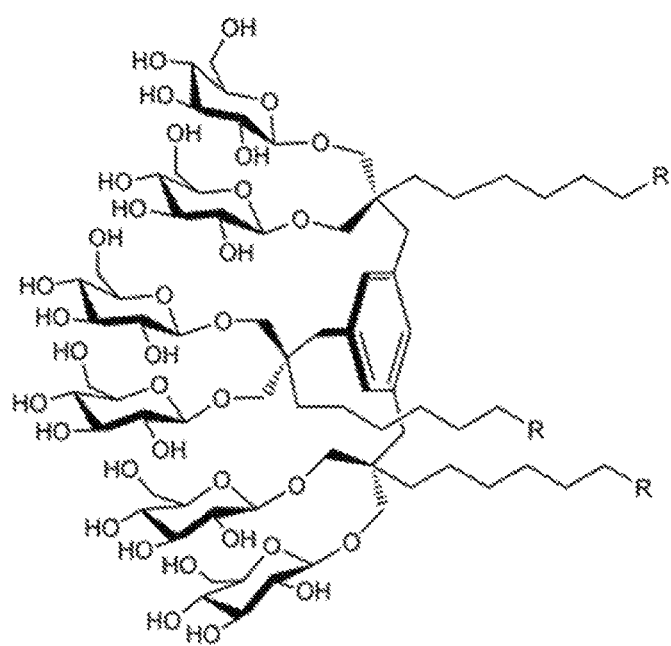
FIG. 2 illustrates a chemical structure of MGAs according to examples of the present invention.

A synthesis scheme of mesitylene-cored glucoside amphiphiles (MGAs) is shown in FIG. 1. Six types of MGAs were synthesized according to the following synthesis methods 1-1 to 1-5 and illustrated in FIG. 2.

<1-1> General Synthesis Procedure of Monoalkylated Diethyl Malonate (Compound A)

Diethyl malonate (5.0 equiv.) was dissolved in a solvent in which THF (20 mL) and DMF (20 mL) were mixed in a ratio of 1:1, and $K_2CO_3$ (5.0 equiv.) was then slowly added thereto in an ice bath. After a mixture was mixed until sufficient gas has been generated, 1-bromoalkane (1.0 equiv.) was added to perform a reaction at 90° C. for 18 hours. After the reaction was finished, a reaction mixture was extracted using diethyl ether, and an organic layer was washed with a 1M HCl aqueous solution (100 mL) and brine (100 mL). The organic layer was dried over anhydrous $Na_2SO_4$, and a solvent was removed using a rotary evaporator. Monoalkylated diethylmalonate (compound A) in an oily liquid state was obtained by silica gel chromatography (EtOAc/hexane).

<1-2> General Synthetic Procedure for Introducing Mesitylene Linker (Step a: Compound A→Compound B)

Monoalkylated diethyl malonate (compound A, 3.3 equiv.) and NaH (4.5 equiv.) were dissolved in a solvent in which THF (15 mL) and DMF (30 mL) were mixed in a ratio of 1:2 in an ice bath. 1,3,5-tris(bromomethyl)benzene (1.0 equiv.) was added to perform a reaction at room temperature for six hours. After determining that the reaction was finished by TLC, a reaction mixture was diluted with diethyl ether (50 mL), and an organic layer was washed by sequentially using a 1M HCl aqueous solution (20 mL) and brine (100 mL). The organic layer was collected and dried using anhydrous $Na_2SO_4$, and a solvent was removed using a rotary evaporator. Compound B in an oily liquid state obtained by silica gel column chromatography (EtOAc/hexane).

<1-3> General Synthetic Procedure for Reducing Ester Using Lithium Aluminum Hydride (LAH) (Step b: Compound B→Compound C)

Compound B (1.0 equiv.) was dissolved in THF (20 mL), and $LiAlH_4$ (7.2 equiv.) was then slowly add thereto in an ice bath. After reacting a reaction mixture at 50° C. for 24 hours, MeOH, water and a 1.0M HCl aqueous solution were sequentially added thereto at 0° C. to eliminate residual reactivity of $LiAlH_4$ which was excessively added, and the reaction mixture was extracted using diethyl ether (2×30 mL). An organic layer was collected to be washed with brine, and dried using anhydrous $Na_2SO_4$. White compound C in a solid state was obtained by silica gel column chromatography (EtOAc/hexane).

<1-4> General Synthetic Procedure for Glycosylation Reaction (Step c: Compound C→Compound D)

This procedure was performed in accordance with a synthesis method (*Chem. Eur. J.* 1996, 2, 1115-1128.) of P. R. Ashton et al. Specifically, compound C as an alcohol derivative, AgOTf (8.0 equiv.) and 2,4,6-collidine (2.0 equiv.) were dissolved in anhydrous $CH_2Cl_2$ (40 mL), and mixed at −45° C. A perbenzoylated glucosylbromide (5.0 equiv.) dissolved in $CH_2Cl_2$ (40 mL) was gradually added to this solution for 10 minutes. After a reaction was performed at −45° C. for 30 minutes, the temperature was slowly raised to 0° C. and a reaction was performed for 90 minutes. After determining the reaction was finished by TLC, pyridine was added to this reaction mixture, and the reaction mixture was then diluted with $CH_2Cl_2$ (40 mL) and precipitates were filtered through celite. An organic solution after filtering was washed by sequentially using a 1M $Na_2S_2O_3$ aqueous solution (40 mL), 1.0M HCl aqueous solution (40 mL) and brine (2×40 mL). After separation of an organic layer, the organic layer was dried using anhydrous $Na_2SO_4$, and a solvent was removed using a rotary evaporator. White compound D in a solid state was obtained by silica gel column chromatography (EtOAc/hexane).

<1-5> General Synthetic Procedure for De-O-Benzoylation Under Zemplen Conditions (Step d; Compound D→Compound E)

This procedure was performed in accordance with a synthetic method (*Chem. Eur. J.* 1996, 2, 1115-1128.) of P. R. Ashton et al. Specifically, O-protected compound D was first dissolved in MeOH, and 0.5M NaOMe, which is a methanolic solution, was added thereto such that the final concentration was 0.05M. After standing the reaction mixture at room temperature for six hours, the reaction mixture was neutralized using an Amberlite IR-120 ($H^+$ form) resin. The resin was removed by filtration, a filtrate was washed with MeOH, and a solvent was removed from the filtrate under vacuum conditions. The residue was purified by silica gel column chromatography (MeOH/$CH_2Cl_2$). After recrystallization by $CH_2Cl_2$/MeOH/diethyl ether, white solid compound E was obtained. Compound E thus obtained is a mesitylene-cored glucoside amphiphile (MGA) compound of the present invention.

<Preparation Example 1> Synthesis of MGA-C10

<1-1> Synthesis of Diethyl 2-decylmalonate

Diethyl 2-decylmalonate (compound 1) was synthesized in a yield of 93% according to the general synthetic procedure of monoalkylated diethyl malonate of Example 1-1. $^1$H NMR (400 MHz, $CDCl_3$): δ 4.22-4.17 (m, 4H), 3.31 (t, J=7.6 Hz, 1H), 1.89-1.87 (m, 2H), 1.30-1.21 (m, 22H), 0.88 (t, J=7.2 Hz, 3H); $^{13}$C NMR (100 MHz, $CDCl_3$): δ 169.8, 61.5, 52.3, 31.1, 29.8, 29.7, 29.5, 29.4, 28.9, 27.5, 22.9, 14.3.

<1-2> Synthesis of Hexaethyl 2,2',2"-(benzene-1,3,5-triyltris(methylene))tris(2-decylmalonate)

Hexaethyl 2,2',2"-(benzene-1,3,5-triyltris(methylene))tris (2-decylmalonate) (compound 7) was synthesized in a yield of 75% according to the general synthetic procedure for introducing a mesitylene linker of Example 1-2. $^1$H NMR (400 MHz, $CDCl_3$): δ 6.68 (s, 3H), 4.22-4.09 (m, 12H), 3.09 (s, 6H), 1.74-1.71 (m, 6H), 1.31-1.20 (m, 66H), 0.88 (t, J=7.2 Hz, 9H); $^{13}$C NMR (100 MHz, $CDCl_3$): δ 171.5, 136.3, 130.5, 61.3, 58.9, 38.4, 32.2, 32.1, 30.0, 29.8, 29.7, 29.5, 24.5, 22.9, 14.3.

<1-3> Synthesis of 2,2',2"-(benzene-1,3,5-triyltris (methylene))tris(2-decylpropane-1,3-diol)

2,2',2"-(benzene-1,3,5-triyltris(methylene))tris(2-decylpropane-1,3-diol) (compound 13) was synthesized in a yield of 74% according to the general synthetic procedure for reducing an ester of Example 1-3 using LAH. $^1$H NMR (400 MHz, $CD_3OD$): δ 6.92 (s, 3H), 3.41 (s, 12H), 2.55 (s, 6H), 1.34-1.12 (m, 54H), 0.89 (t, J=6.8 Hz, 9H); $^{13}$C NMR (100 MHz, $CD_3OD$): δ 138.6, 131.8, 66.2, 44.3, 38.1, 33.3, 32.4, 32.1, 31.1, 31.0, 30.7, 24.3, 23.9, 14.7.

<1-4> Synthesis of MGA-C10a

MGA-C10a was synthesized in a yield of 50% according to the general synthetic procedure for a glycosylation reaction of Example 1-4. Due to aggregation of a compound, broad peaks were observed in low resolution in a $^1$H NMR spectrum of this compound dissolved in $CDCl_3$ or DMSO-$d_6$, and thus precise analysis was impossible.

<1-5> Synthesis of MGA-C10

Figure 3:
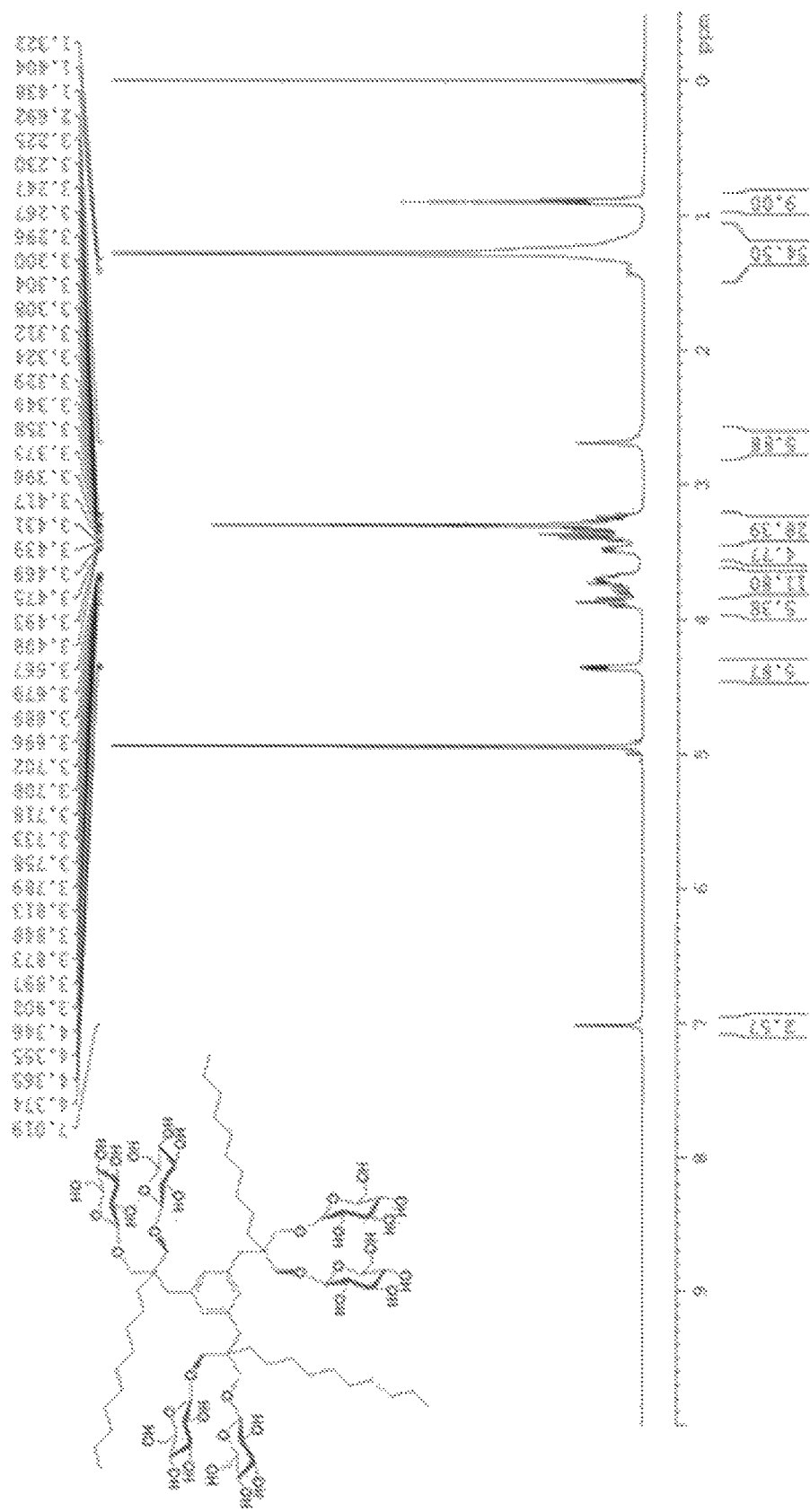
FIG. 3 illustrates a $^1$H NMR spectrum of MGA-C10.
Figure 4:
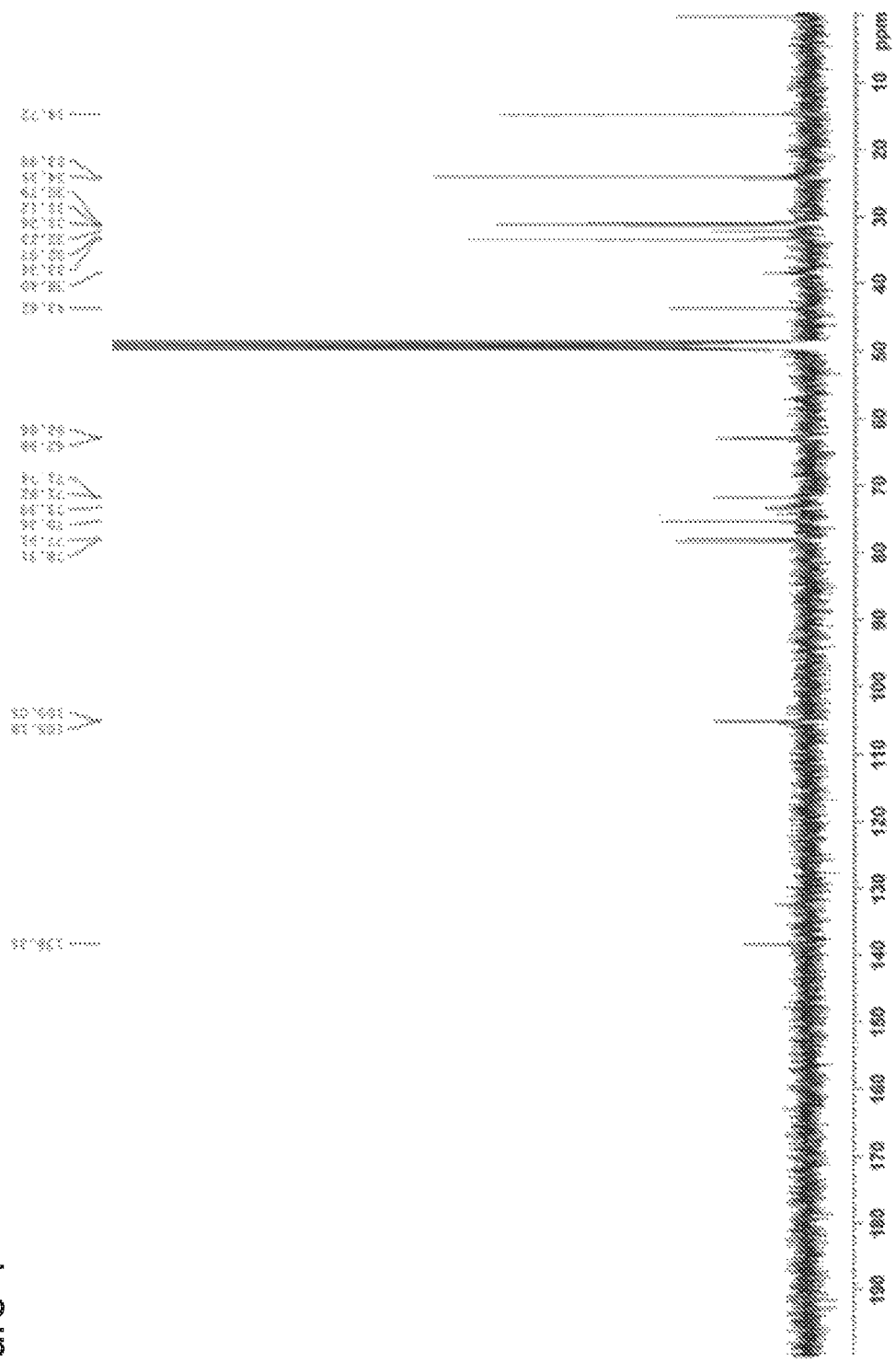
FIG. 4 illustrates a $^{13}$C NMR spectrum of MGA-C10.

MGA-C10 was synthesized in a yield of 94% according to the general synthetic procedure for de-O-benzoylation of Example 1-5. A $^1$H NMR spectrum is shown in FIG. 3, and a $^{13}$C NMR spectrum is shown in FIG. 4. $^1$H NMR (400 MHz, $CD_3OD$): δ 7.02 (s, 3H), 4.38-4.35 (m, 6H), 3.90-3.87 (m, 6H), 3.81-3.67 (m, 12H), 3.51-3.46 (m, 6H), 3.42-3.22 (m, 12H), 2.69 (s, 6H), 1.41-1.16 (m, 54H), 0.90 (t, J=7.2 Hz, 9H); $^{13}$C NMR (100 MHz, $CD_3OD$): δ 138.4, 105.2, 105.1, 78.3, 77.9, 75.4, 73.4, 71.8, 71.7, 62.9, 43.6, 38.4, 33.3, 32.9, 32.2, 31.3, 31.1, 30.8, 24.4, 23.9, 14.7; HRMS (EI): calcd. for $C_{84}H_{150}O_{36}[M+Na]^+$ 1757.9805, found: 1757.9810.

<Preparation Example 2> Synthesis of MGA-C11

<2-1> Synthesis of Diethyl 2-undecylmalonate

Diethyl 2-undecylmalonate (compound 2) was synthesized in a yield of 90% according to the general synthetic procedure of monoalkylated diethyl malonate of Example 1-1. $^1$H NMR (400 MHz, $CDCl_3$): δ4.23-4.16 (m, 4H), 3.31 (t, J=7.6 Hz, 1H), 1.89-1.87 (m, 2H), 1.31-1.25 (m, 24H), 0.88 (t, J=7.2 Hz, 3H); $^{13}$C NMR (100 MHz, $CDCl_3$): δ 169.8, 61.5, 52.3, 32.1, 29.8, 29.7, 29.6, 29.4, 28.9, 27.5, 22.9, 14.3.

<2-2> Synthesis of Hexaethyl 2,2',2"-(benzene-1,3, 5-triyltris(methylene))tris(2-undecylmalonate)

Hexaethyl 2,2',2"-(benzene-1,3,5-triyltris(methylene))tris (2-decylmalonate) (compound 8) was synthesized in a yield of 76% according to the general synthetic procedure for introducing a mesitylene linker of Example 1-2. $^1$H NMR (400 MHz, $CDCl_3$): δ 6.68 (s, 3H), 4.22-4.09 (m, 12H), 3.09 (s, 6H), 1.74-1.71 (m, 6H), 1.31-1.20 (m, 72H), 0.88 (t, J=7.2 Hz, 9H); $^{13}$C NMR (100 MHz, $CDCl_3$): δ 171.5, 136.3, 130.5, 61.3, 58.9, 38.4, 32.1, 30.0, 29.9, 29.8, 29.7, 29.6, 24.5, 22.9, 14.3.

<2-3> Synthesis of 2,2',2"-(benzene-1,3,5-triyltris (methylene))tris(2-undecylpropane-1,3-diol)

2,2',2"-(benzene-1,3,5-triyltris(methylene))tris(2-decylpropane-1,3-diol) (compound 14) was synthesized in a yield of 75% according to the general synthetic procedure for reducing an ester of Example 1-3 using LAH. $^1$H NMR (400 MHz, $CD_3OD$): δ 6.92 (s, 3H), 3.41 (s, 12H), 2.55 (s, 6H), 1.34-1.12 (m, 60H), 0.89 (t, J=6.8 Hz, 9H); $^{13}$C NMR (100 MHz, $CD_3OD$): δ 138.6, 131.8, 66.2, 44.3, 38.1, 33.3, 32.4, 32.1, 31.1, 31.0, 30.7, 24.3, 23.9, 14.7.

<2-4> Synthesis of MGA-C11a

MGA-C11a was synthesized in a yield of 51% according to the general synthetic procedure for a glycosylation reaction of Example 1-4. Due to aggregation of a compound, broad peaks were observed in low resolution in a $^1$H NMR spectrum of this compound dissolved in $CDCl_3$ or DMSO-$d_6$, and thus precise analysis was impossible.

<2-5> Synthesis of MGA-C11

Figure 5:
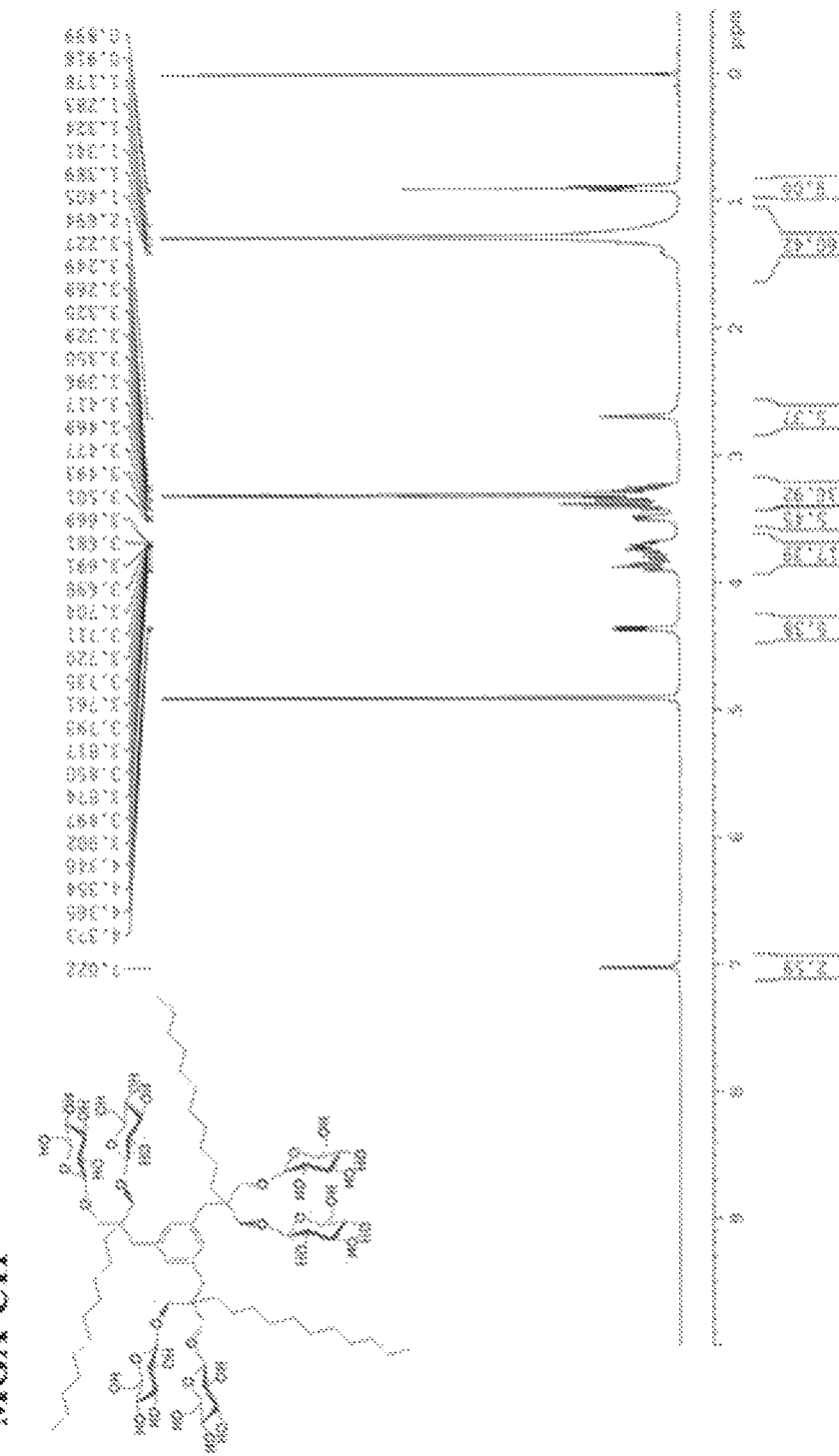
FIG. 5 illustrates a $^1$H NMR spectrum of MGA-C11.
Figure 6:
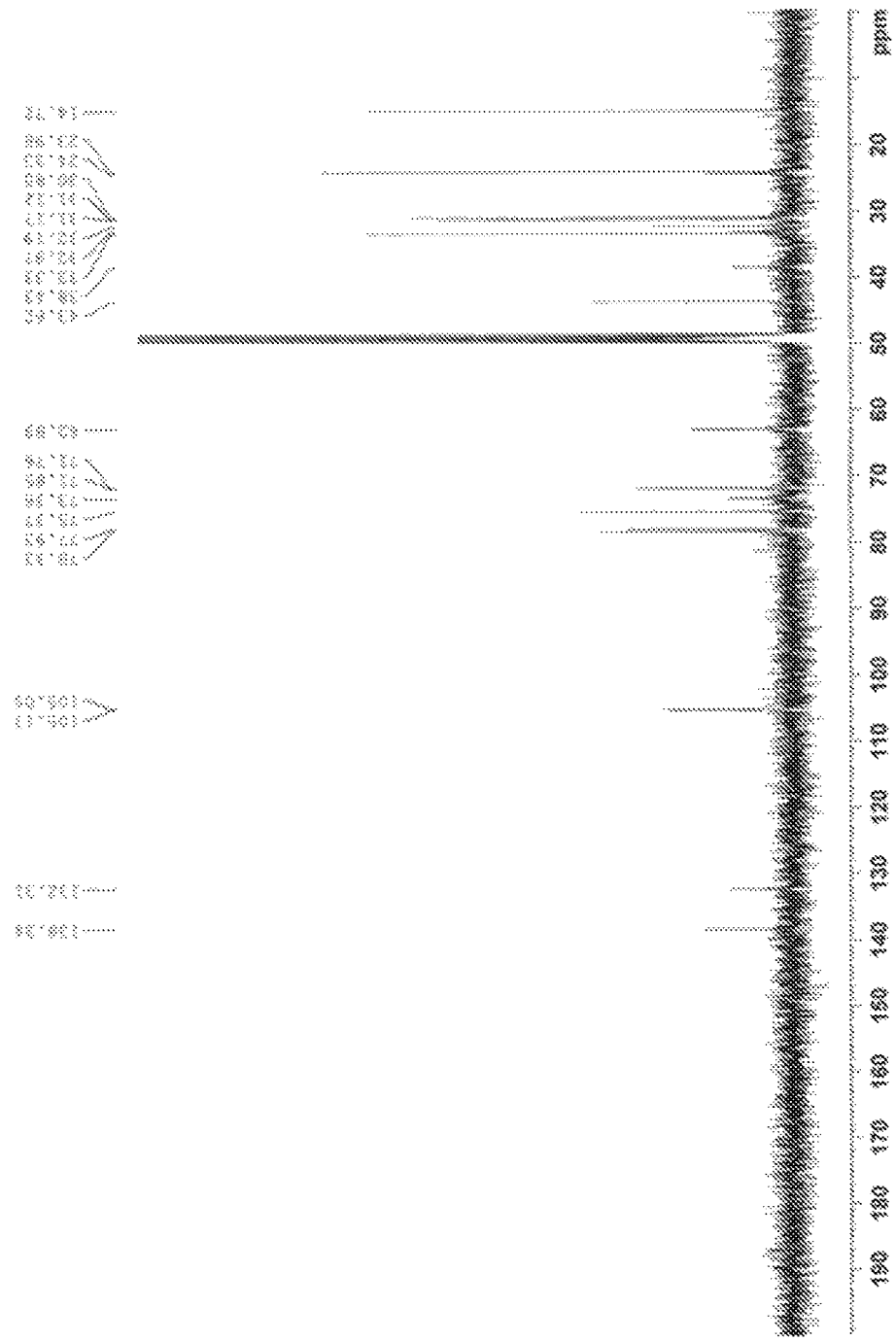
FIG. 6 illustrates a $^{13}$C NMR spectrum of MGA-C11.

MGA-C11 was synthesized in a yield of 92% according to the general synthetic procedure for de-O-benzoylation of Example 1-5. A $^1$H NMR spectrum is shown in FIG. 5, and a $^{13}$C NMR spectrum is shown in FIG. 6. $^1$H NMR (400 MHz, CD$_3$OD): δ 7.02 (s, 3H), 4.38-4.35 (m, 6H), 3.90-3.87 (m, 6H), 3.81-3.67 (m, 12H), 3.51-3.46 (m, 6H), 3.42-3.22 (m, 12H), 2.69 (s, 6H), 1.41-1.16 (m, 60H), 0.90 (t, J=7.2 Hz, 9H); $^{13}$C NMR (100 MHz, CD$_3$OD): δ 138.3, 132.3, 105.2, 105.1, 78.3, 77.9, 75.4, 73.4, 71.9, 71.8, 62.9, 43.6, 38.4, 33.3, 32.9, 32.2, 31.2, 31.1, 30.8, 24.3, 23.9, 14.7; HRMS (EI): calcd. for C$_{87}$H$_{156}$O$_{36}$[M+Na]$^+$ 1801.0308, found: 1801.0337.

<Preparation Example 3> Synthesis of MGA-C12

<3-1> Synthesis of Diethyl 2-dodecylmalonate

Diethyl 2-dodecylmalonate (compound 3) was synthesized in a yield of 91% according to the general synthetic procedure of monoalkylated diethyl malonate of Example 1-1. $^1$H NMR (400 MHz, CDCl$_3$): δ 4.22-4.16 (m, 4H), 3.31 (t, J=7.6 Hz, $^1$H), 1.90-1.87 (m, 2H), 1.30-1.25 (m, 26H), 0.87 (t, J=7.2 Hz, 3H); $^{13}$C NMR (100 MHz, CDCl$_3$): δ 169.9, 61.5, 52.3, 32.1, 29.9, 29.7, 29.6, 29.5, 29.4, 28.9, 27.5, 22.9, 14.4.

<3-2> Synthesis of Hexaethyl 2,2',2''-(benzene-1,3,5-triyltris(methylene))tris(2-dodecylmalonate)

Hexaethyl 2,2',2''-(benzene-1,3,5-triyltris(methylene))tris(2-dodecylmalonate) (compound 9) was synthesized in a yield of 73% according to the general synthetic procedure for introducing a mesitylene linker of Example 1-2. $^1$H NMR (400 MHz, CDCl$_3$): δ 6.68 (s, 3H), 4.22-4.09 (m, 12H), 3.09 (s, 6H), 1.74-1.71 (m, 6H), 1.31-1.20 (m, 78H), 0.88 (t, J=7.2 Hz, 9H); $^{13}$C NMR (100 MHz, CDCl$_3$): δ 171.5, 136.3, 130.5, 61.3, 58.9, 38.4, 32.1, 30.0, 29.9, 29.8, 29.7, 29.6, 24.5, 22.9, 14.3.

<3-3> Synthesis of 2,2',2''-(benzene-1,3,5-triyltris(methylene))tris(2-dodecylpropane-1,3-diol)

2,2',2''-(benzene-1,3,5-triyltris(methylene))tris(2-dodecylpropane-1,3-diol) (compound 15) was synthesized in a yield of 72% according to the general synthetic procedure for reducing an ester of Example 1-3 using LAH. $^1$H NMR (400 MHz, CD$_3$OD): δ 6.92 (s, 3H), 3.41 (s, 12H), 2.55 (s, 6H), 1.34-1.12 (m, 66H), 0.89 (t, J=6.8 Hz, 9H); $^{13}$C NMR (100 MHz, CD$_3$OD): δ 138.6, 131.8, 66.2, 44.3, 38.1, 33.3, 32.4, 32.1, 31.1, 31.0, 30.7, 24.3, 23.9, 14.7.

<3-4> Synthesis of MGA-C12a

MGA-C12a was synthesized in a yield of 51% according to the general synthetic procedure for a glycosylation reaction of Example 1-4. Due to aggregation of a compound, broad peaks were observed in low resolution in a $^1$H NMR spectrum of this compound dissolved in CDCl$_3$ or DMSO-d$_6$, and thus precise analysis was impossible.

<3-5> Synthesis of MGA-C12

Figure 7:
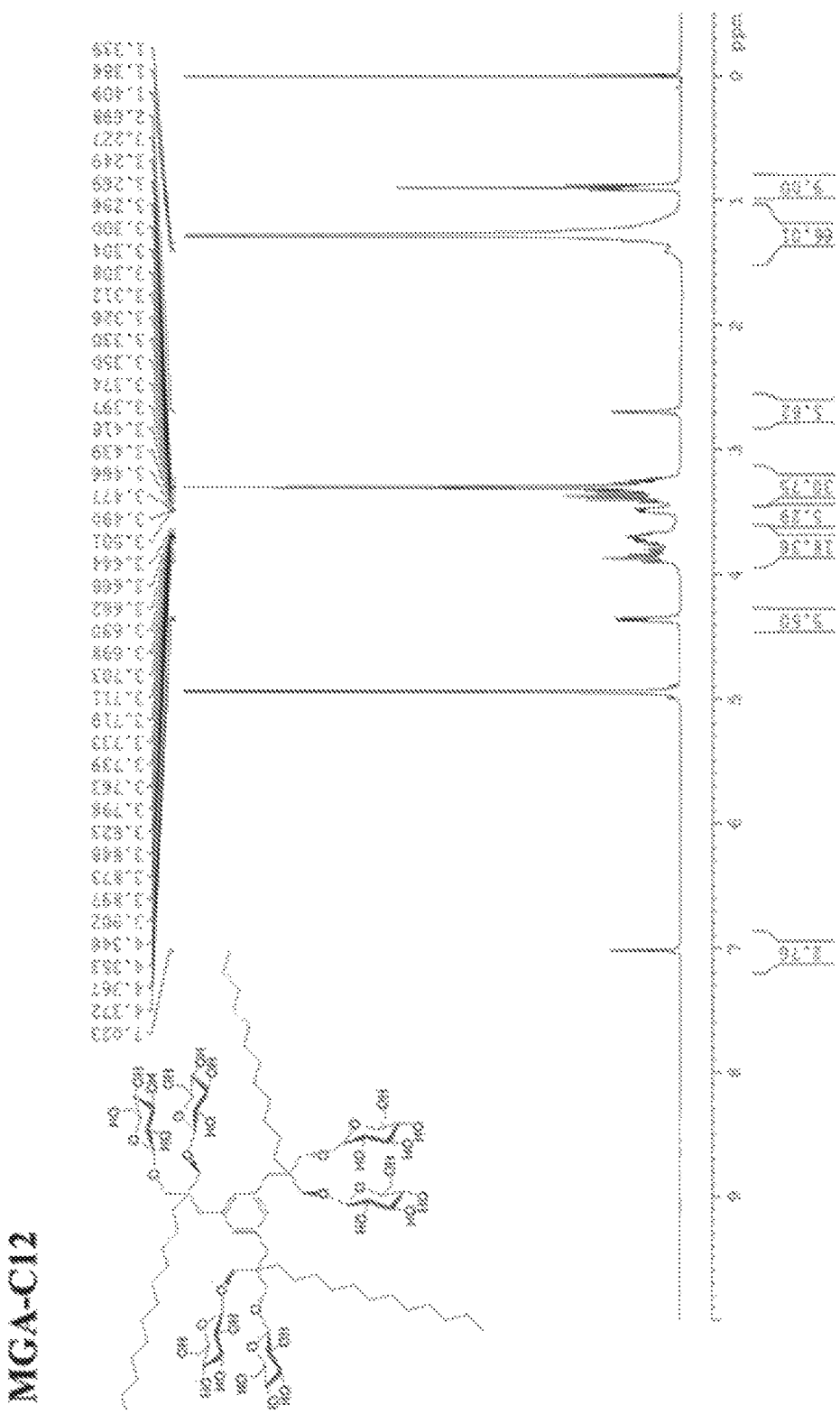
FIG. 7 illustrates a $^1$H NMR spectrum of MGA-C12.
Figure 8:
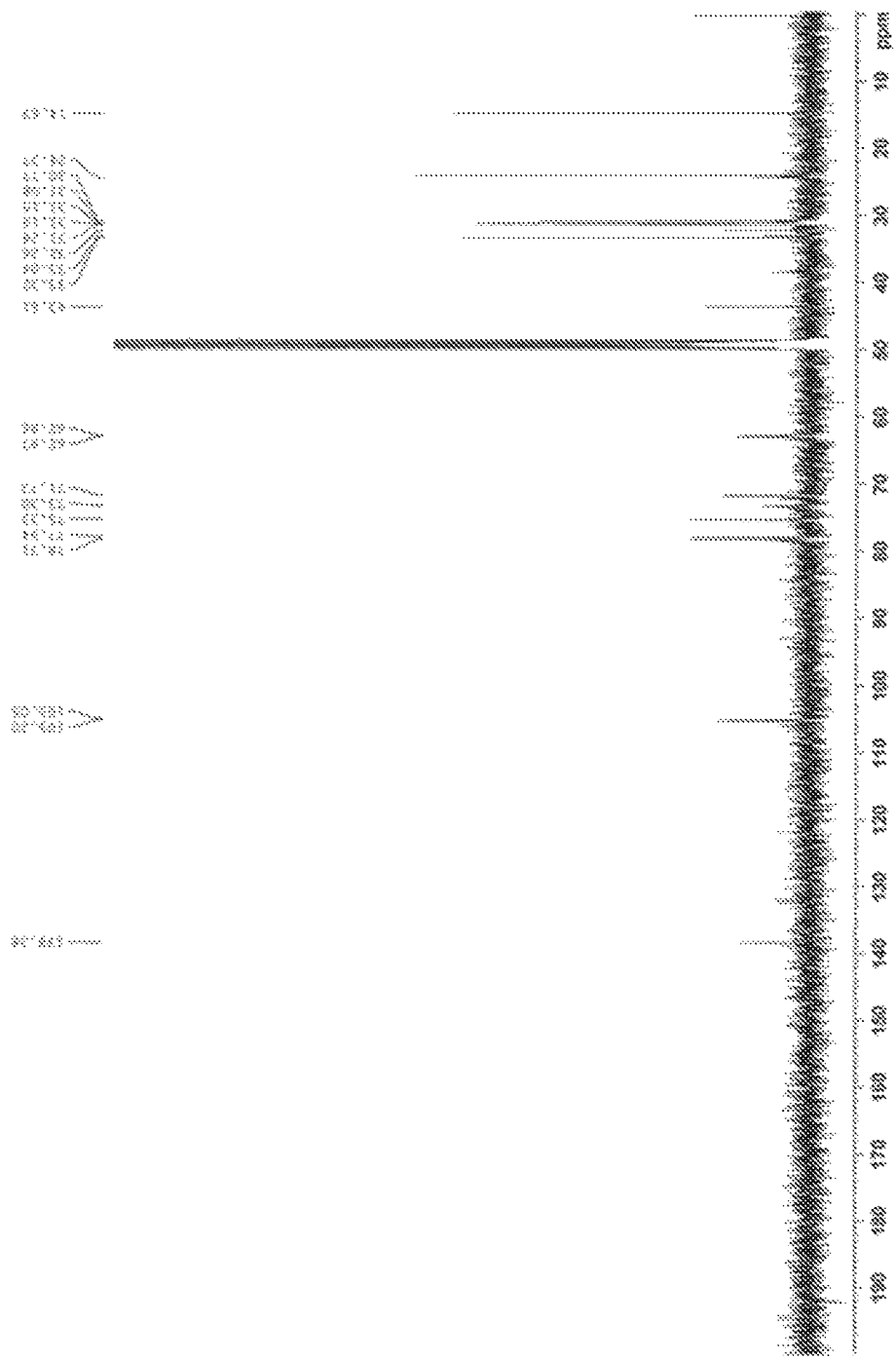
FIG. 8 illustrates a $^{13}$C NMR spectrum of MGA-C12.

MGA-C12 was synthesized in a yield of 94% according to the general synthetic procedure for de-O-benzoylation of Example 1-5. A $^1$H NMR spectrum is shown in FIG. 7, and a $^{13}$C NMR spectrum is shown in FIG. 8. $^1$H NMR (400 MHz, CD$_3$OD): δ 7.02 (s, 3H), 4.38-4.35 (m, 6H), 3.90-3.87 (m, 6H), 3.81-3.67 (m, 12H), 3.51-3.46 (m, 6H), 3.42-3.22 (m, 12H), 2.69 (s, 6H), 1.41-1.16 (m, 66H), 0.90 (t, J=7.2 Hz, 9H); $^{13}$C NMR (100 MHz, CD$_3$OD): δ 138.4, 105.2, 105.1, 78.3, 77.9, 75.3, 73.3, 71.7, 62.9, 43.6, 33.3, 33.0, 31.3, 31.2, 31.1, 30.1, 24.4, 14.7; HRMS (EI): calcd. for C$_9$H$_{161}$O$_{36}$[M+Na]$^+$ 1842.0700, found: 1841.0668.

<Preparation Example 4> Synthesis of MGA-C13

<4-1> Synthesis of Diethyl 2-tridecylmalonate

Diethyl 2-tridecylmalonate (compound 4) was synthesized in a yield of 88% according to the general synthetic procedure of monoalkylated diethyl malonate of Example 1-1. $^1$H NMR (400 MHz, CDCl$_3$): δ 4.22-4.16 (m, 4H), 3.31 (t, J=7.6 Hz, $^1$H), 1.90-1.87 (m, 2H), 1.30-1.25 (m, 28H), 0.87 (t, J=7.2 Hz, 3H); $^{13}$C NMR (100 MHz, CDCl$_3$): δ 169.9, 61.5, 52.3, 32.1, 29.9, 29.8, 29.7, 29.6, 29.5, 29.4, 28.9, 27.5, 22.9, 14.4, 14.3.

<4-2> Synthesis of Hexaethyl 2,2',2''-(benzene-1,3,5-triyltris(methylene))tris(2-tridecylmalonate)

Hexaethyl 2,2',2''-(benzene-1,3,5-triyltris(methylene))tris(2-tridecylmalonate) (compound 10) was synthesized in a yield of 70% according to the general synthetic procedure for introducing a mesitylene linker of Example 1-2. $^1$H NMR (400 MHz, CDCl$_3$): δ 6.68 (s, 3H), 4.22-4.09 (m, 12H), 3.09 (s, 6H), 1.74-1.71 (m, 6H), 1.31-1.20 (m, 84H), 0.88 (t, J=7.2 Hz, 9H); $^{13}$C NMR (100 MHz, CDCl$_3$): δ 171.5, 136.3, 130.5, 61.3, 58.9, 38.4, 32.1, 30.0, 29.9, 29.8, 29.7, 29.6, 24.5, 22.9, 14.3.

<4-3> Synthesis of 2,2',2''-(benzene-1,3,5-triyltris(methylene))tris(2-tridecylpropane-1,3-diol)

2,2',2''-(benzene-1,3,5-triyltris(methylene))tris(2-tridecylpropane-1,3-diol) (compound 16) was synthesized in a yield of 74% according to the general synthetic procedure for reducing an ester of Example 1-3 using LAH. $^1$H NMR (400 MHz, CD$_3$OD): δ 6.92 (s, 3H), 3.41 (s, 12H), 2.55 (s, 6H), 1.34-1.12 (m, 72H), 0.89 (t, J=6.8 Hz, 9H); $^{13}$C NMR (100 MHz, CD$_3$OD): δ 138.6, 131.8, 66.2, 44.3, 38.1, 33.3, 32.4, 32.1, 31.1, 31.0, 30.7, 24.3, 23.9, 14.7.

<4-4> Synthesis of MGA-C13a

MGA-C13a was synthesized in a yield of 47% according to the general synthetic procedure for a glycosylation reaction of Example 1-4. Due to aggregation of a compound, broad peaks were observed in low resolution in a $^1$H NMR spectrum of this compound dissolved in CDCl$_3$ or DMSO-d$_6$, and thus precise analysis was impossible.

<4-5> Synthesis of MGA-C13

Figure 9:
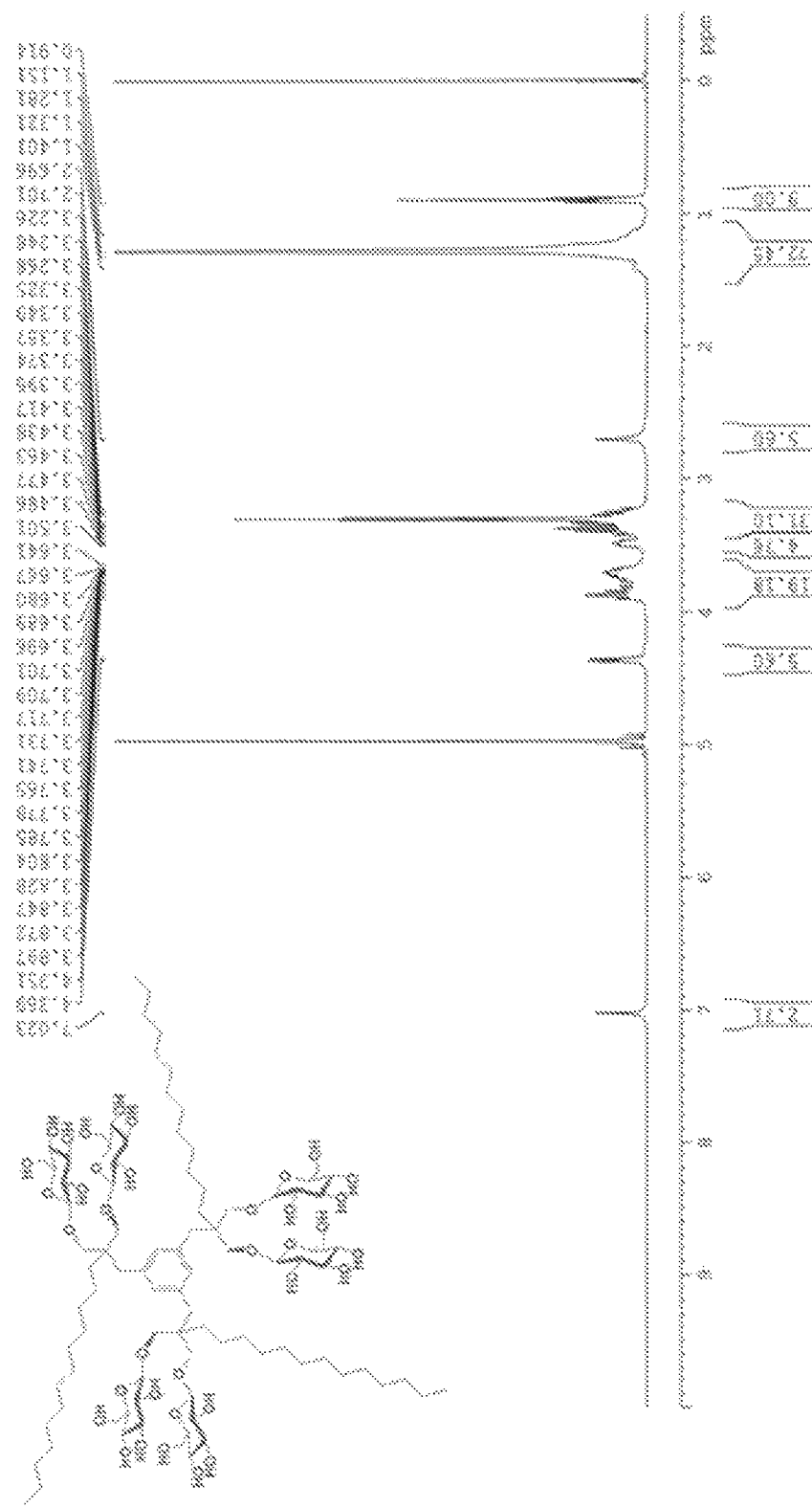
FIG. 9 illustrates a $^1$H NMR spectrum of MGA-C13.
Figure 10:
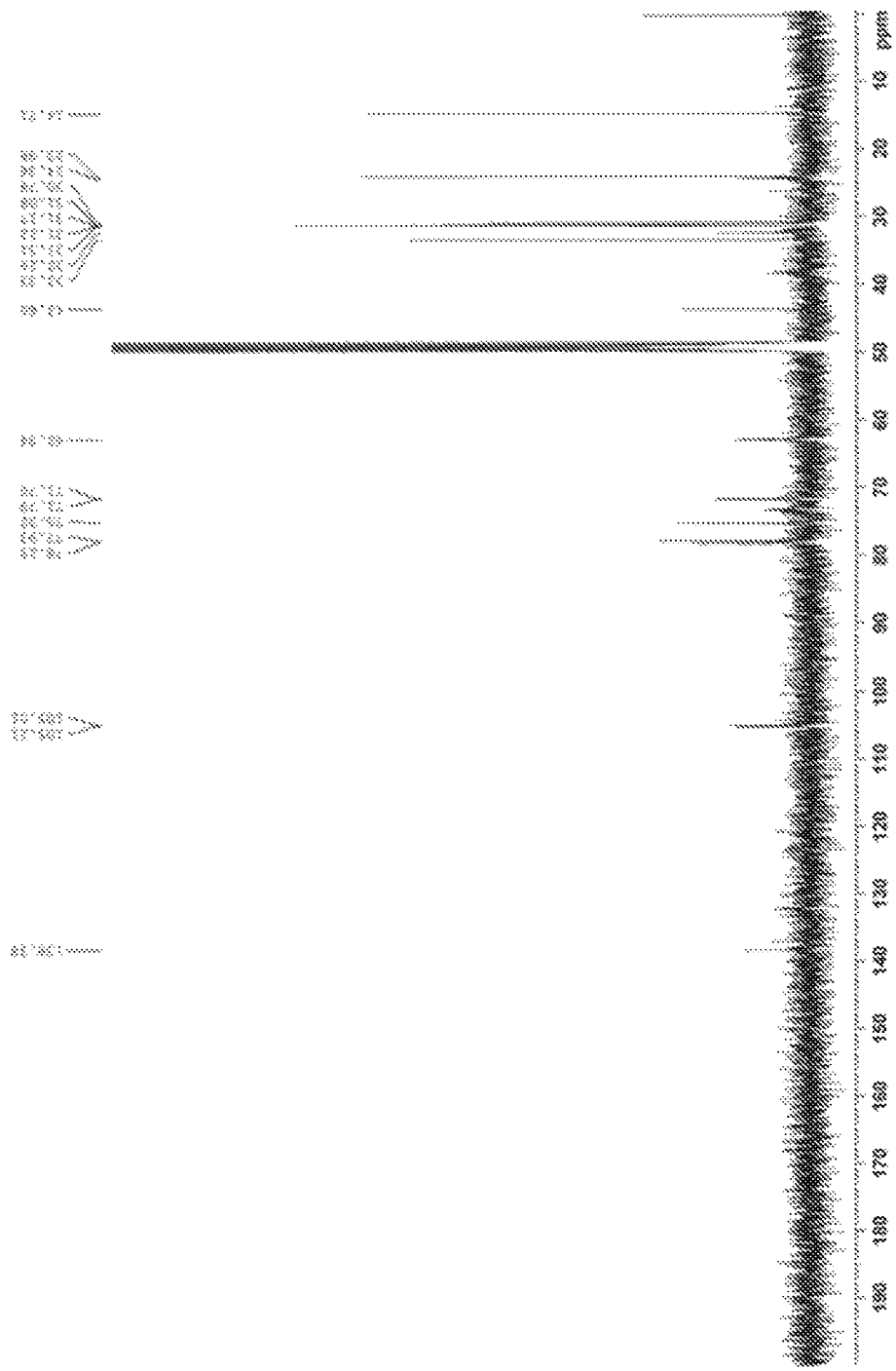
FIG. 10 illustrates a $^{13}$C NMR spectrum of MGA-C13.

MGA-C13 was synthesized in a yield of 91% according to the general synthetic procedure for de-O-benzoylation of Example 1-5. A $^1$H NMR spectrum is shown in FIG. 9, and a $^{13}$C NMR spectrum is shown in FIG. 10. $^1$H NMR (400 MHz, CD$_3$OD): δ 7.02 (s, 3H), 4.38-4.35 (m, 6H), 3.90-3.87 (m, 6H), 3.81-3.67 (m, 12H), 3.51-3.46 (m, 6H), 3.42-3.22 (m, 12H), 2.69 (s, 6H), 1.41-1.16 (m, 72H), 0.90 (t, J=7.2 Hz, 9H); $^{13}$C NMR (100 MHz, CD$_3$OD): δ 138.4, 105.2, 105.1, 78.3, 77.9, 75.3, 71.8, 71.7, 62.9, 43.6, 33.3, 31.3, 31.2, 31.1, 30.8, 24.4, 23.9, 14.7; HRMS (EI): calcd. for $C_{93}H_{168}O_{36}[M+Na]^+$ 1885.1247, found: 1885.0898.

<Preparation Example 5> Synthesis of MGA-C14

<5-1> Synthesis of Diethyl 2-tetradecylmalonate

Diethyl 2-tetradecylmalonate (compound 5) was synthesized in a yield of 89% according to the general synthetic procedure of monoalkylated diethyl malonate of Example 1-1. $^1$H NMR (400 MHz, $CDCl_3$): δ 4.22-4.16 (m, 4H), 3.31 (t, J=7.6 Hz, $^1$H), 1.90-1.87 (m, 2H), 1.30-1.25 (m, 30H), 0.87 (t, J=7.2 Hz, 3H); $^{13}$C NMR (100 MHz, $CDCl_3$): δ 169.9, 61.5, 52.3, 32.1, 29.9, 29.7, 29.6, 29.5, 29.4, 28.9, 27.5, 22.9, 14.4.

<5-2> Synthesis of Hexaethyl 2,2',2"-(benzene-1,3,5-triyltris(methylene))tris(2-tetradecylmalonate)

Hexaethyl 2,2',2"-(benzene-1,3,5-triyltris(methylene))tris(2-tetradecylmalonate) (compound 11) was synthesized in a yield of 73% according to the general synthetic procedure for introducing a mesitylene linker of Example 1-2. $^1$H NMR (400 MHz, $CDCl_3$): δ 6.68 (s, 3H), 4.22-4.09 (m, 12H), 3.09 (s, 6H), 1.74-1.71 (m, 6H), 1.31-1.20 (m, 90H), 0.88 (t, J=7.2 Hz, 9H); $^{13}$C NMR (100 MHz, $CDCl_3$): δ 171.5, 136.3, 130.5, 61.3, 58.9, 38.4, 32.1, 30.0, 29.9, 29.8, 29.7, 29.6, 24.5, 22.9, 14.3.

<5-3> Synthesis of 2,2',2"-(benzene-1,3,5-triyltris(methylene))tris(2-tetradecylpropane-1,3-diol)

2,2',2"-(benzene-1,3,5-triyltris(methylene))tris(2-tetradecylpropane-1,3-diol) (compound 17) was synthesized in a yield of 70% according to the general synthetic procedure for reducing an ester of Example 1-3 using LAH. $^1$H NMR (400 MHz, $CD_3OD$): δ 6.92 (s, 3H), 3.41 (s, 12H), 2.55 (s, 6H), 1.34-1.12 (m, 78H), 0.89 (t, J=6.8 Hz, 9H); $^{13}$C NMR (100 MHz, $CD_3OD$): δ 138.6, 131.8, 66.2, 44.3, 38.1, 33.3, 32.4, 32.1, 31.1, 31.0, 30.7, 24.3, 23.9, 14.7.

<5-4> Synthesis of MGA-C14a

MGA-C14a was synthesized in a yield of 48% according to the general synthetic procedure for a glycosylation reaction of Example 1-4. Due to aggregation of a compound, broad peaks were observed in low resolution in a $^1$H NMR spectrum of this compound dissolved in $CDCl_3$ or DMSO-$d_6$, and thus precise analysis was impossible.

<5-5> Synthesis of MGA-C14

Figure 11:
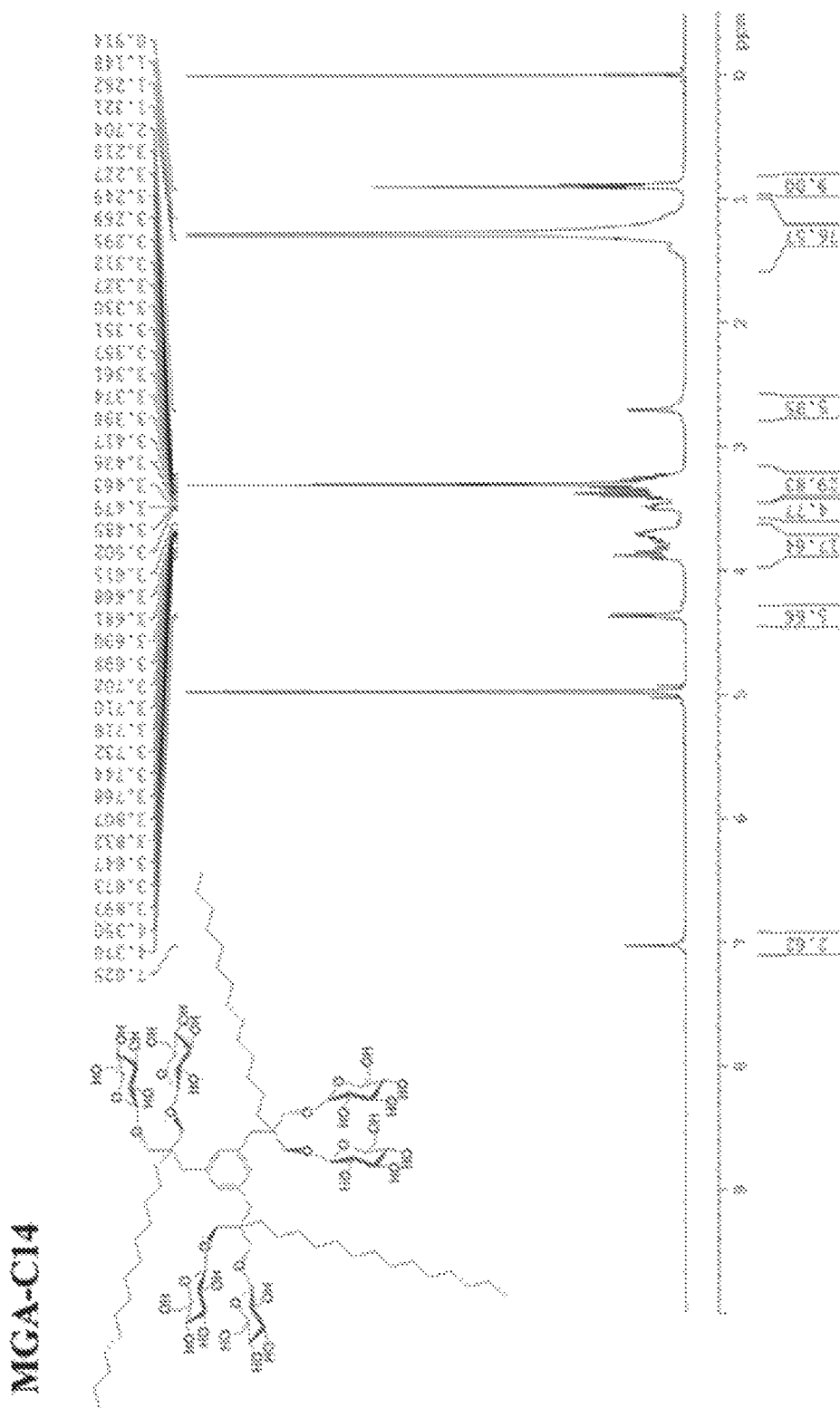
FIG. 11 illustrates a $^1$H NMR spectrum of MGA-C14.
Figure 12:
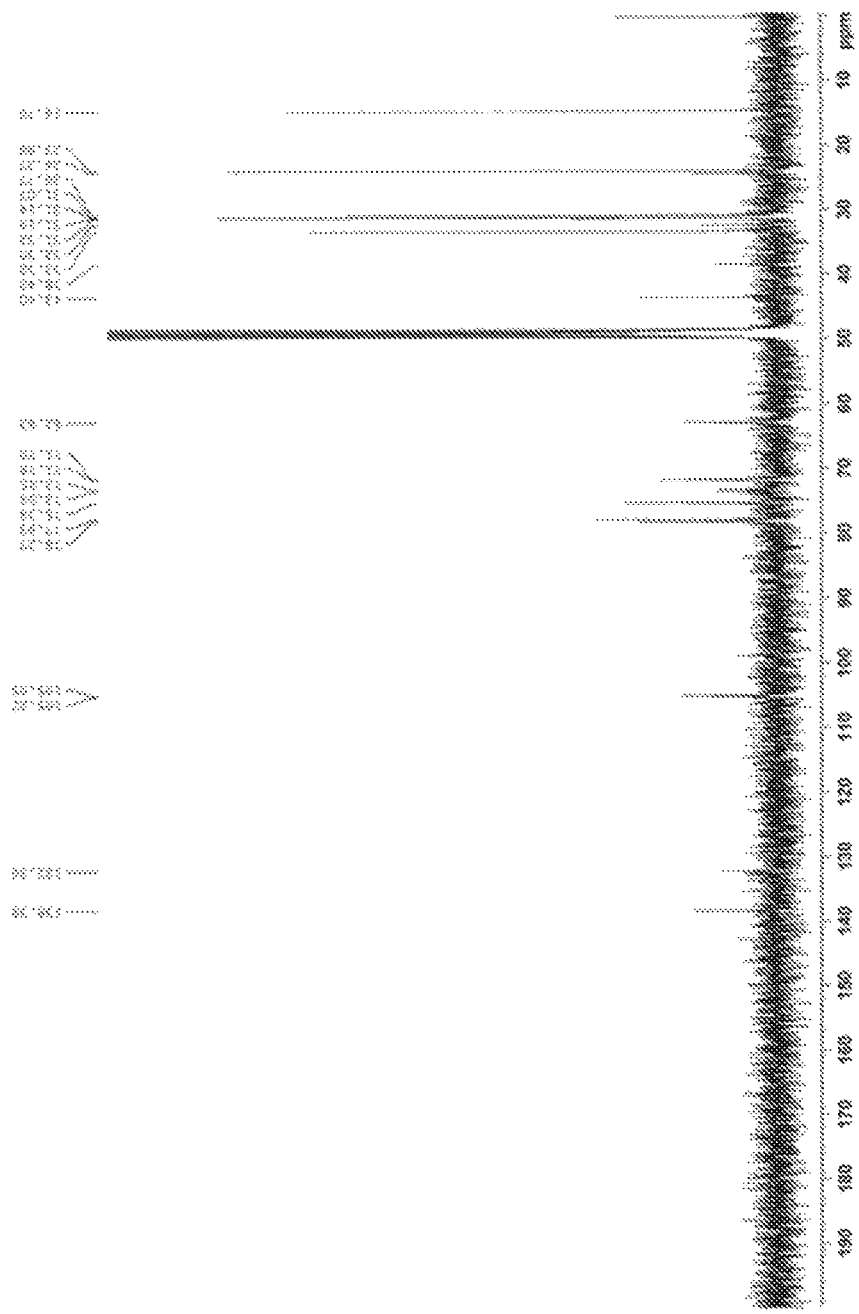
FIG. 12 illustrates a $^{13}$C NMR spectrum of MGA-C14.

MGA-C14 was synthesized in a yield of 93% according to the general synthetic procedure for de-O-benzoylation of Example 1-5. A $^1$H NMR spectrum is shown in FIG. 11, and a $^{13}$C NMR spectrum is shown in FIG. 12. $^1$H NMR (400 MHz, $CD_3OD$): δ 7.02 (s, 3H), 4.38-4.35 (m, 6H), 3.90-3.87 (m, 6H), 3.81-3.67 (m, 12H), 3.51-3.46 (m, 6H), 3.42-3.22 (m, 12H), 2.69 (s, 6H), 1.41-1.16 (m, 78H), 0.90 (t, J=7.2 Hz, 9H); $^{13}$C NMR (100 MHz, $CD_3OD$): δ 168.4, 132.3, 105.2, 105.1, 78.3, 77.9, 75.3, 73.5, 73.3, 71.8, 71.7, 62.8, 43.6, 38.4, 33.4, 32.3, 31.3, 31.2, 31.1, 30.8, 24.4, 23.9, 14.7; HRMS (EI): calcd. for $C_{96}H_{174}O_{36}[M+Na]^+$ 1927.1717, found: 1927.1675.

<Preparation Example 6> Synthesis of MGA-C15

<6-1> Synthesis of Diethyl 2-pentadecylmalonate

Diethyl 2-pentadecylmalonate (compound 6) was synthesized in a yield of 86% according to the general synthetic procedure of monoalkylated diethyl malonate of Example 1-1. $^1$H NMR (400 MHz, $CDCl_3$): δ 4.22-4.16 (m, 4H), 3.31 (t, J=7.6 Hz, $^1$H), 1.90-1.87 (m, 2H), 1.30-1.25 (m, 32H), 0.87 (t, J=7.2 Hz, 3H); $^{13}$C NMR (100 MHz, $CDCl_3$): δ 169.9, 61.5, 52.3, 32.1, 29.9, 29.8, 29.7, 29.6, 29.5, 29.4, 28.9, 27.5, 22.9, 14.4, 14.3.

<6-2> Synthesis of Hexaethyl 2,2',2"-(benzene-1,3,5-triyltris(methylene))tris(2-pentadecylmalonate)

Hexaethyl 2,2',2"-(benzene-1,3,5-triyltris(methylene))tris(2-pentadecylmalonate) (compound 12) was synthesized in a yield of 71% according to the general synthetic procedure for introducing a mesitylene linker of Example 1-2. $^1$H NMR (400 MHz, $CDCl_3$): δ 6.68 (s, 3H), 4.22-4.09 (m, 12H), 3.09 (s, 6H), 1.74-1.71 (m, 6H), 1.31-1.20 (m, 96H), 0.88 (t, J=7.2 Hz, 9H); $^{13}$C NMR (100 MHz, $CDCl_3$): δ 171.5, 136.3, 130.5, 61.3, 58.9, 38.4, 32.1, 30.0, 29.9, 29.8, 29.7, 29.6, 24.5, 22.9, 14.3.

<6-3> Synthesis of 2,2',2"-(benzene-1,3,5-triyltris(methylene))tris(2-pentadecylpropane-1,3-diol)

2,2',2"-(benzene-1,3,5-triyltris(methylene))tris(2-pentadecylpropane-1,3-diol) (compound 18) was synthesized in a yield of 72% according to the general synthetic procedure for reducing an ester of Example 1-3 using LAH. $^1$H NMR (400 MHz, $CD_3OD$): δ 6.92 (s, 3H), 3.41 (s, 12H), 2.55 (s, 6H), 1.34-1.12 (m, 84H), 0.89 (t, J=6.8 Hz, 9H); $^{13}$C NMR (100 MHz, $CD_3OD$): δ 138.6, 131.8, 66.2, 44.3, 38.1, 33.3, 32.4, 32.1, 31.1, 31.0, 30.7, 24.3, 23.9, 14.7.

<6-4> Synthesis of MGA-C15a

MGA-C15a was synthesized in a yield of 45% according to the general synthetic procedure for a glycosylation reaction of Example 1-4. Due to aggregation of a compound, broad peaks were observed in low resolution in a $^1$H NMR spectrum of this compound dissolved in $CDCl_3$ or DMSO-$d_6$, and thus precise analysis was impossible.

<6-5> Synthesis of MGA-C15

Figure 13:
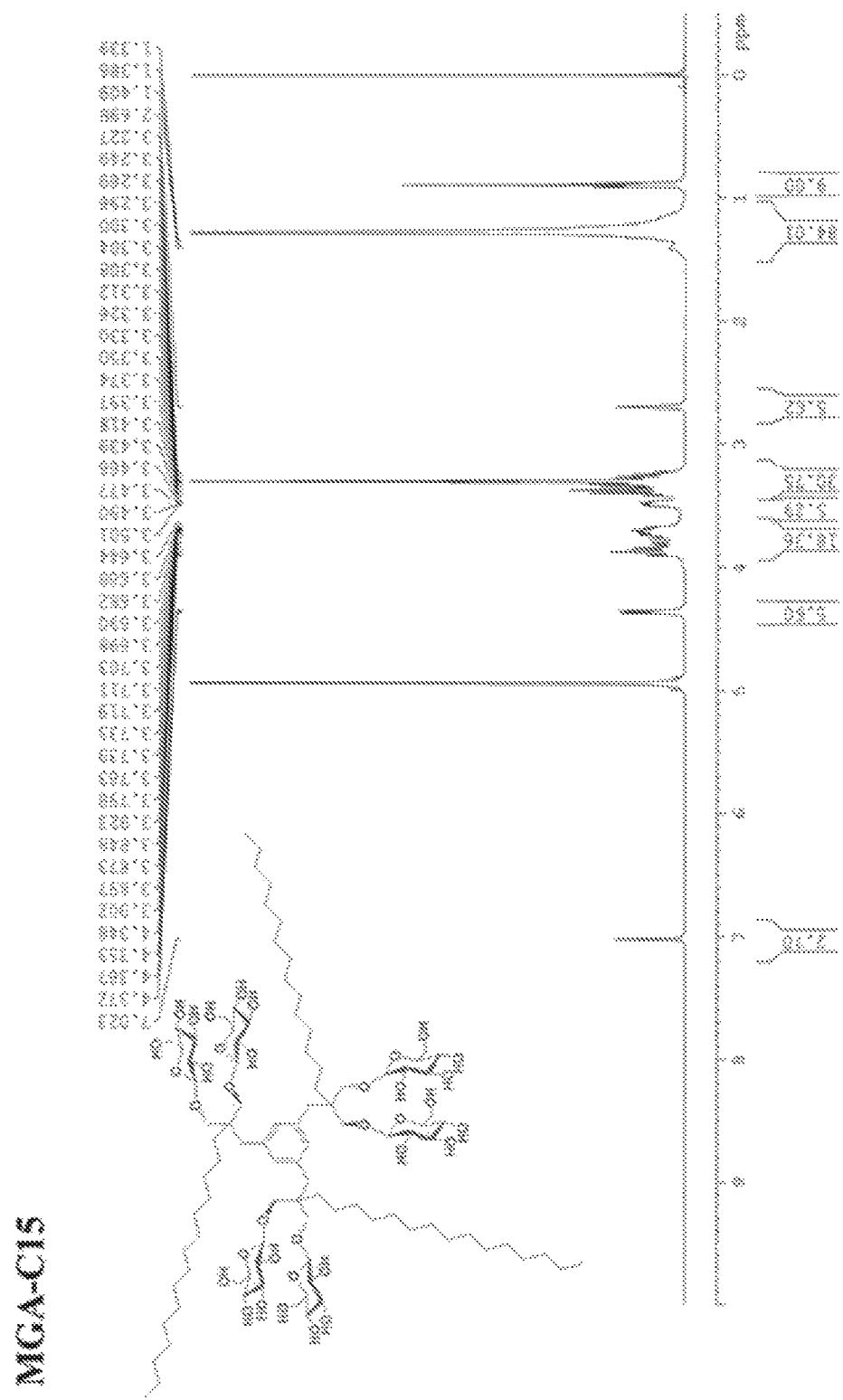
FIG. 13 illustrates a $^1$H NMR spectrum of MGA-C15.
Figure 14:
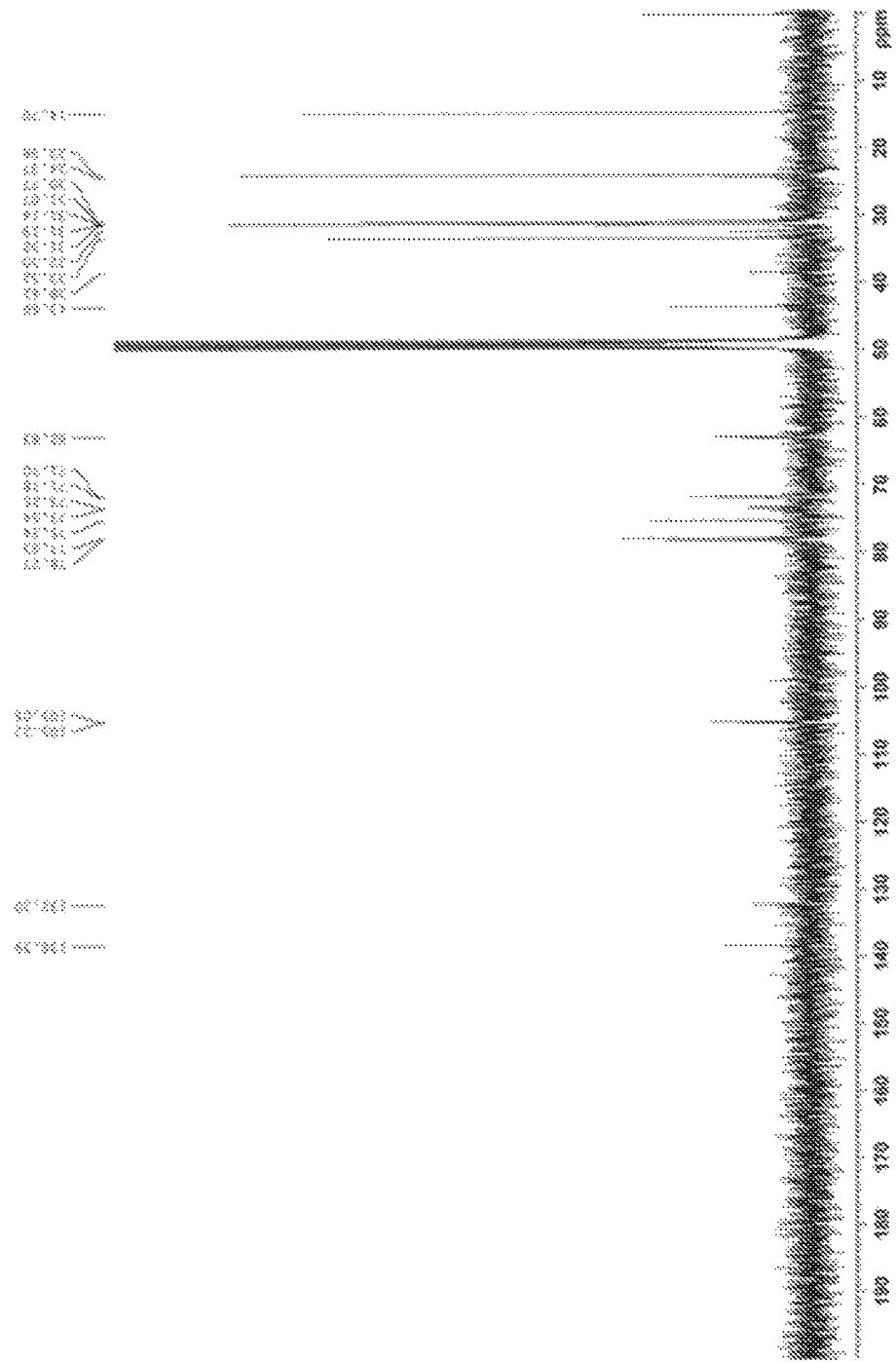
FIG. 14 illustrates a $^{13}$C NMR spectrum of MGA-C15.

MGA-C15 was synthesized in a yield of 92% according to the general synthetic procedure for de-O-benzoylation of Example 1-5. A $^1$H NMR spectrum is shown in FIG. 13, and a $^{13}$C NMR spectrum is shown in FIG. 14. $^1$H NMR (400 MHz, $CD_3OD$): δ 7.02 (s, 3H), 4.38-4.35 (m, 6H), 3.90-3.87 (m, 6H), 3.81-3.67 (m, 12H), 3.51-3.46 (m, 6H), 3.42-3.22 (m, 12H), 2.69 (s, 6H), 1.41-1.16 (m, 84H), 0.90 (t, J=7.2 Hz, 9H); $^{13}$C NMR (100 MHz, $CD_3OD$): δ 168.4, 132.3, 105.2, 105.1, 78.3, 77.9, 75.3, 73.5, 73.3, 71.8, 71.7, 62.8, 43.6, 38.4, 33.3, 32.2, 31.3, 31.2, 31.1, 30.8, 24.4, 23.9, 14.7; HRMS (EI): calcd. for $C_{99}H_{180}O_{36}[M+Na]^+$ 1969.2186, found: 1968.2430.

<Comparative Example 1> Comparison of MGAs and XGAs

Figure 15A:
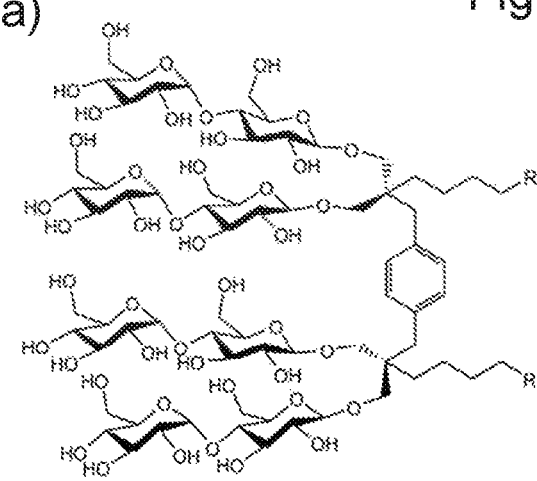
FIGS. 15(a) and 15(b) illustrate a chemical structure of (a) XMAs and (b) XGAs.
Figure 15B:
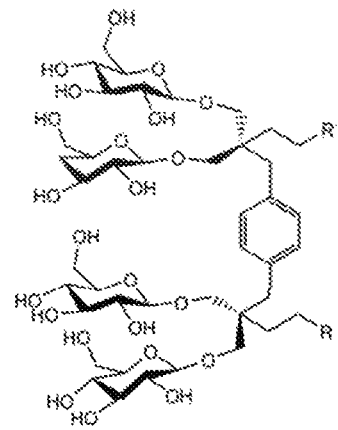

The inventors of the present invention have previously developed xylene-linked maltoside amphiphiles (XMAs)

and xylene-linked glucoside amphiphiles (XGAs) having a xylene linker (see FIG. 15). XGAs/XMAs and MGAs are structurally distinct from one another because XGAs/XMAs have two hydrophobic groups while MGAs prepared according to Example 1 have three hydrophobic groups, and XGAs/XMAs have four hydrophilic groups while MGAs have six hydrophilic groups. More practical differences between the two types of compounds are described as follows.

First, since XGAs are more difficult to synthesize than XMAs, the overall synthetic yield for XGAs is 10% or less. The main cause is that a synthetic yield of XGAs in a glycosylation step is 15% or less. That is, synthetic efficiency of XGAs is lower than that of XMAs.

Second, XGAs has very low water-solubility, and an XGA (XGA-C7) with a $C_7$ alkyl chain in particular has a water-solubility of 1% or less. Therefore, in order to use XGAs in membrane protein research, XGA-C4, XGA-C5 and XGA-C6 with a short alkyl chain are only usable. Generally, amphiphilic molecules having a short alkyl chain are ineffective at stabilizing membrane proteins.

Third, XGAs do not show an excellent effect on solubilization and stabilization of membrane proteins. There is a limitation on control of membrane proteins because XGAs tend to form large self-aggregates with a diameter of 150 to 200 nm (see Table 1).

TABLE 1

| Detergent | MW | CMC (mM) | CMC (wt %) | $R_h$ (nm) |
|---|---|---|---|---|
| XGA-C4 | 1015.1 | ~0.8 | ~0.081 | 170 ± 11.6 |
| XGA-C5 | 1043.1 | ~0.8 | ~0.083 | 199 ± 7.1 |
| XGA-C6 | 1071.2 | ~0.8 | ~0.086 | 177 ± 7.9 |

The inventors of the present invention developed glucoside amphiphiles using a mesitylene linker instead of using a xylene linker in order to overcome this limitation, and compounds thus obtained are MGAs. Since a central structure was changed from xylene to mesitylene, three alkyl chains and three branched diglucosides are introduced around a central benzene ring to enable formation of a high density structure.

MGAs can be prepared without difficulty by a protocol consisting of five synthetic steps, and the overall synthetic yield thereof is about 25%, that is, they have a higher yield than XGAs.

Furthermore, it should be noted that MGAs have dramatically increased water-solubility as compared to XGAs. It was observed that MGA-C15 with a C15 alkyl chain had a high water-solubility of 20% or more in the case of MGAs, while in the case of XGAs, only 1% or less of XGA-C7 with a C7 alkyl chain was dissolved in water.

A similar tendency is observed when MGAs are compared with XMAs which are dialkylated-maltoside compounds. That is, XMAs with a maximum alkyl chain length of Cu can be used to maintain excellent water-solubility. It should be noted that XMAs (glucose units: 8) has a higher number of glucose units than MGA (glucose units: 6).

Accordingly, it is expected from these results that MGAs are more advantageous in membrane protein research because MGAs possess a structure with higher water-solubility than XMAs and XGAs.

<Experimental Example 1> Characteristics of MGAs

In order to determine characteristics of MGAs of Preparation Examples 1 to 5 synthesized using the synthesis method of Example 1, a molecular weight (M.W.) and a critical micelle concentration (CMC) of MGAs and a hydrodynamic radius (Rh) of a micelle formed by MGAs were measured.

Specifically, a CMC was measured by a fluorophorescent encapsulation method using diphenylhexatriene (DPH) and an Rh of a micelle formed by each formulation (1.0 wt %) was measured using a dynamic light scattering (DLS) experiment. The measurement results are compared with DDM which is a conventional amphiphilic molecule (detergent) and shown in Table 2.

TABLE 2

| Detergent | M.W. | CMC (μM) | CMC (wt %) | $R_h$ (nm) |
|---|---|---|---|---|
| MGA-C10 | 1736.1 | ~8 | ~0.0014 | 2.9 ± 0.01 |
| MGA-C11 | 1778.2 | ~5 | ~0.009 | 3.0 ± 0.04 |
| MGA-C12 | 1820.3 | ~3.5 | ~0.0006 | 3.1 ± 0.03 |
| MGA-C13 | 1862.3 | ~3 | ~0.0006 | 3.2 ± 0.03 |
| MGA-C14 | 1904.4 | ~2 | ~0.0004 | 3.4 ± 0.04 |
| MGA-C15 | 1946.5 | ~1.5 | ~0.0003 | 3.6 ± 0.02 |
| DDM | 510.1 | ~170 | ~0.0087 | 3.4 ± 0.02 |

The CMC values (1.5-8.0 μM) of all MGAs are markedly lower than the CMC value (~170 μM) of DDM. Since micelles can be easily formed with only a small amount of MGAs, the same effect as DDM or greater can be exhibited with only a small amount of MGAs. Moreover, the CMC values of MGAs decrease as an alkyl chain length increases, specifically, MGA-C10 with the shortest alkyl chain has the highest CMC value (~8.0 μM) and MGA-C15 with the longest alkyl chain has the lowest CMC value (~1.5 μM).

The size of micelles formed by MGAs are smaller than or the same as that of micelles formed by DDM. This is considered to be due to large hydrophilic groups (i.e., three branched diglucosides). Furthermore, a micelle size has a tendency to increase as an alkyl chain length increases. This is assumed to be due to a gradual change of a geometrical structure, from a conical shape to a cylindrical shape.

Figure 16:
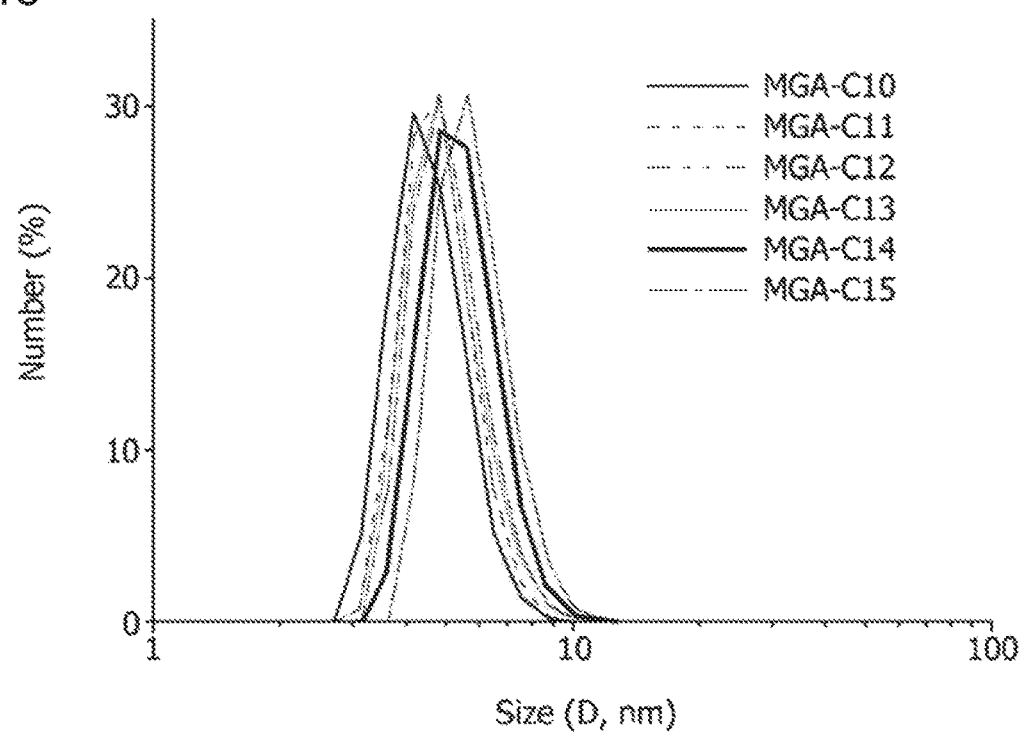
FIG. 16 illustrates a particle size distribution of micelles formed by MGAs.

Further, a result of measuring a particle size distribution of micelles formed by MGAs is shown in FIG. 16. Since the particle size distribution of micelles formed by MGAs showed a single set of narrow peaks, it was determined that micelle homogeneity was high (see FIG. 16).

It can be seen from these results that, MGAs of the present invention have lower CMC values than DDM to allow easy formation of micelles with only a small amount of MGAs, and thus have a higher tendency to self-assembly than DDM. MGAs are similar to existing DDM in terms of a geometrical structure of molecules because the size of micelles formed by MGAs is similar to that of micelles formed by DDM, and micelles formed by MGAs have high micelle homogeneity.

<Experimental Example 2> Evaluation of UapA Membrane Protein Structure Stabilization Ability of MGAs An experiment for measuring the structural stability of uric acid-xanthine/$H^+$ symporter (UapA) solubilized in MGAs in an aqueous solution was performed. The structural stability of UapA was measured using a CPM assay, and was measured at MGAs and DDM concentrations of (a) CMC+ 0.04 wt %, or (b) CMC+0.2 wt %.

Specifically, a UapA protein is a uric acid-xanthine/$H^+$ symporter in *Aspergillus nidulans*. Protein stability was measured by fluorescence spectroscopy using N-[4-(7-diethylamino-4-methyl-3-coumarinyl)phenyl]maleimide (CPM)

which is a sulfhydryl-specific fluorophore. A free sulfhydryl group of a cysteine residue is in the interior of a protein, but becomes accessible to a solvent upon protein unfolding. CPM becomes fluorescent by a reaction with the free thiol, and thus provides as a protein unfolding sensor. In order to measure thermal stability, first, UapAG411V1-11 was expressed in the *Saccharomyces cerevisiae* FGY217 strain by fusion with GFP, and separated in a sample buffer (20 mM Tris (pH 7.5), 150 mM NaCl, 0.03% DDM and 1 mM xanthine) according to a method described in a research article (*Mol. Membr. Biol.* 2013, 30, 32-42) by J. Leung et al. A UapA protein was concentrated to about 10 mg/ml using a 100 kDa molecular weight cut-off filter (Millipore). The concentrated protein was diluted to a ratio of 1:150 with each buffer including DDM or MGA (MGA-C10, MGA-C11, MGA-C12, MGA-C13, MGA-C14 or MGA-C15) at a concentration of CMC+0.04 wt % or CMC+0.2 wt % in a Greiner 96-well plate. A CPM dye (Invitrogen) stored in DMSO (Sigma) was diluted with a dye buffer (20 mM Tris (pH 7.5), 150 mM NaCl, 0.03% DDM and 5 mM EDTA), and 3 μl of the diluted dye was added to each protein sample. The reaction mixture was incubated at 40° C. for 120 minutes. Fluorescence emission was monitored using a microplate spectrofluorometer, with an excitation wavelength at 387 nm and an emission wavelength at 463 nm. Relative maximum fluorescence was used to calculate a percentage of relative folded protein remaining after 120 minutes at 40° C. Relative unfolded proteins were plotted against time using GraphPad Prism.

Figures 17A, 17B:
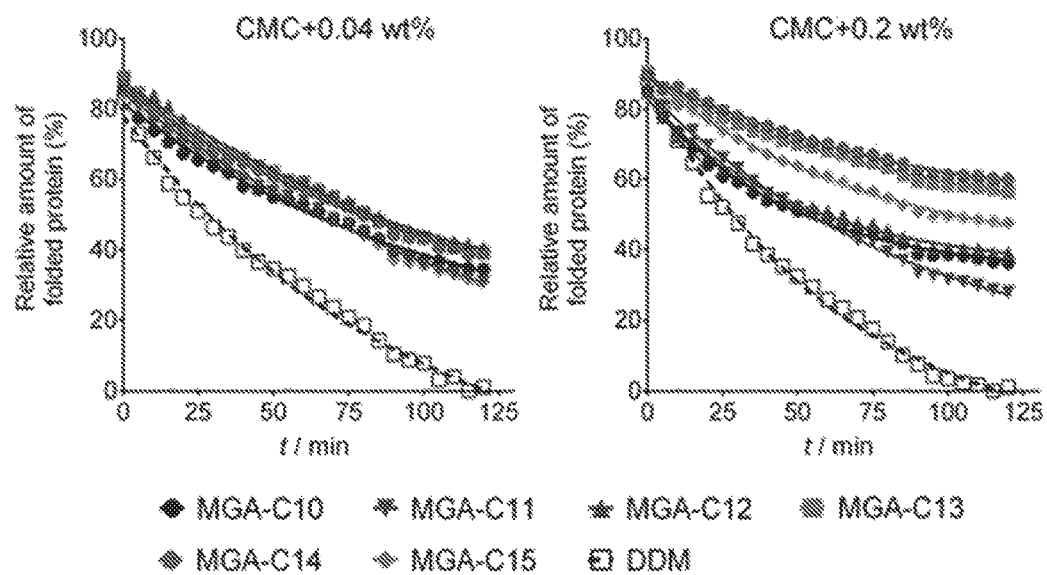
FIGS. 17(a) and 17(b) illustrate a result of measuring the structural stability of UapA according to MGAs (MGA-C10, MGA-C11, MGA-C12, MGA-C13, MGA-C14 and MGA-C15) or DDM in an aqueous solution using a CPM assay:
17(a) a concentration of MGAs or DDM is CMC+0.04 wt %; and
17(b) a concentration of MGAs or DDM is CMC+0.2 wt %.

As can be seen from the result shown in FIG. 17, all of the six MGAs were more excellent than DDM in maintaining a folded state of UapA at a concentration of CMC+0.04 wt % or CMC+0.2 wt %. However, a difference in effect found between MGAs at a concentration of CMC+0.2 wt %. In MGAs, MGA-C13 and MGA-C14 had the highest effect, followed by MGA-C15. Other MGAs (MGA-C10, MGA-C11 and MGA-C12) with relatively short alkyl chains were less effective than the above-described MGAs, but still higher than DDM.

It can be seen from these results that, since MGAs have a higher effect of maintaining a folded state of UapA than DDM, MGAs have a good ability to stabilize the structure of UapA, and thus can be used to stabilize membrane proteins.

<Experimental Example 3> Evaluation of MelB Membrane Protein Structure Stabilization Ability of MGAs An experiment for measuring the structural stability of *Salmonella typhimurium* melibiose permease (MelB$_{St}$) according to MGAs in an aqueous solution was performed. After MelB$_{St}$ proteins were extracted from a membrane using MGAs or DDM, the amount and structure of extracted proteins were analyzed by SDS-PAGE and western blotting. The concentration of used amphiphiles was 1.5 wt %, and proteins were extracted at four different temperatures of 0, 45, 55 and 65° C. to evaluate both the protein extraction efficiency and stabilizing ability of a compound. A membrane sample which had not been treated with MGAs or DDM was used as a control group.

Specifically, MelB$_{St}$ stability solubilized in DDM or MGAs was evaluated according to a method described in 2010 in a research article (P. S. Chae et al., *Nat. Methods* 2010, 7, 1003-1008.) by the inventors of the present invention. Proteins (MelB$_{St}$) were produced using plasmid pK95ΔAHB/WT MelB$_{St}$/CH10 encoding the wild-type MelB with a 6-His tag at the C-terminus and *Salmonella typhimurium* DW2 cells (ΔmelB and ΔlacZY). Cell growth and membrane preparation was performed according to a method described in a research article (*Nat. Commun.* 2014, 5, 3009) by A. S. Ethayathulla, et al. A protein assay was carried out using a Micro BCA kit (Thermo Scientific, Rockford, Ill.). In order to measure protein solubilization, a membrane sample (final protein concentration was 10 mg/mL) containing MelB$_{St}$ was incubated with a solubilization buffer (20 mM sodium phosphate, pH 7.5, 200 mM NaCl, 10% glycerol and 20 mM melibiose) and 1.5% (w/v) DDM or MGA (MGA-C10, MGA-C11, MGA-C12, MGA-C13, MGA-C14 or MGA-C15) at four different temperatures of 0, 45, 55 and 65° C. for 90 minutes. After ultracentrifugation at 355,590 g in a Beckman Optima™ MAX Ultracentrifuge using a TLA-100 rotor for 45 min at 4° C., 20 μg of a protein was separated by SDS-16% PAGE and immunoblotted with a Penta-His-HRP antibody (Qiagen, Germantown, Md.). MelB$_{St}$ was measured by an ImageQuant LAS 4000 Biomolecular Imager (GE Healthcare Life Sciences) using a SuperSignal West Pico chemiluminescent substrate.

Figure 18A:
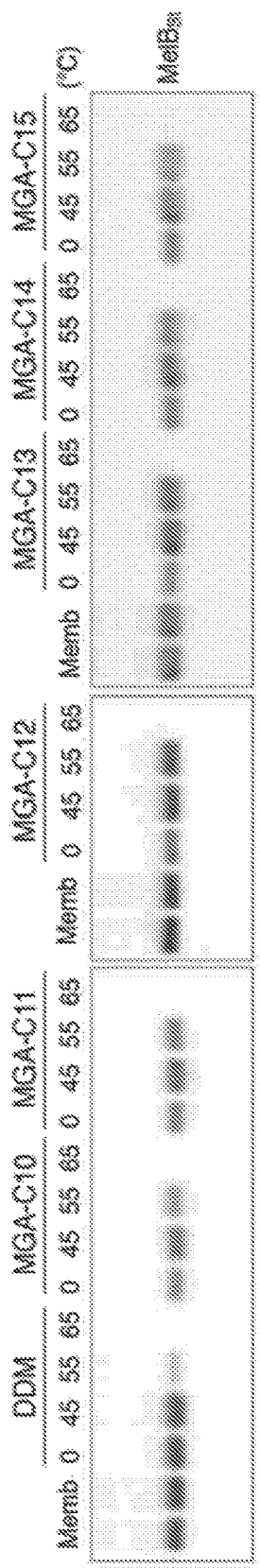
FIGS. 18(a) and 18(b) illustrate a result of measuring an amount of MelB proteins extracted at four different temperatures of 0, 45, 55 and 65° C. using MGAs (MGA-C10, MGA-C11, MGA-C12, MGA-C13, MGA-C14 and MGA-C15) or DDM at a concentration of 1.5 wt %:
18(a) SDS-PAGE and Western Blotting results showing an amount of MelB proteins extracted using each amphiphilic molecule; and
18(b) a histogram in which an amount of MelB proteins extracted using each amphiphilic molecule is expressed by a percentage (%) of the total protein amount existing in a membrane sample (Memb) that is not treated with amphiphiles.
Figure 18B:
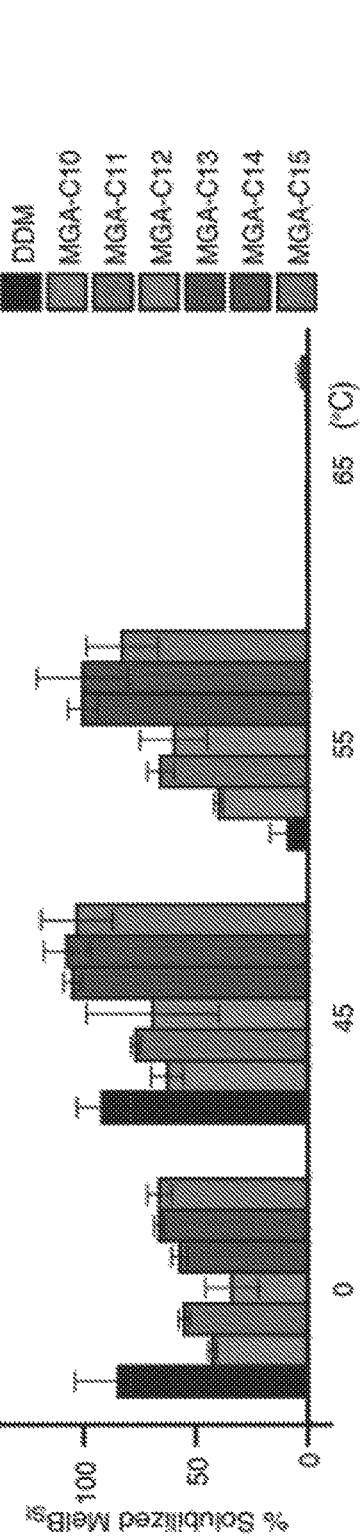

As can be seen from the result shown in FIG. 18, in the case of DDM, high protein extraction efficiency was found at 0° C. and 45° C., but almost no protein was observed at a temperature of 55° C. or more. This indicates that MelB$_{St}$ extracted by DDM denatured or aggregated to disappear in the solution as the temperature increases. However, in the case of MGA-C13, MGA-C14 and MGA-C15, protein extraction efficiency increased at 45° C. and 55° C., and thereby MGA-C13, MGA-C14 and MGA-C15 reached the same level of protein extraction efficiency as DDM at 45° C., and exhibited higher MelB$_{St}$ extraction ability than DDM at 55° C. In particular, MGA-C13 and MGA-C14 had excellent extraction efficiency of about 90 to 100%. It can be seen from these results that the MelB$_{St}$ stabilizing ability of MGA-C13 and MGA-C14 is remarkably higher than that of DDM.

Figure 19B:
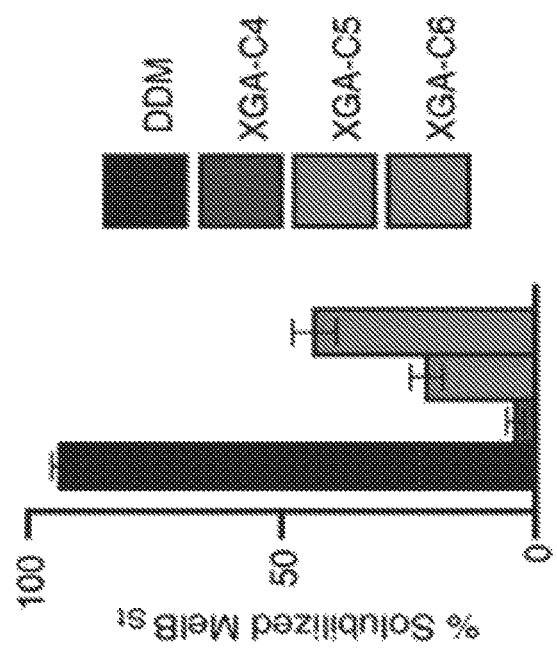
FIGS. 19(a), 19(b) and 19(c) illustrate a result of measuring an amount of MelB proteins extracted using XGAs (XGA-C4, XGA-C5 and XGA-C6) or DDM at a concentration of 1.5 wt %:
19(a) SDS-PAGE and Western Blotting results of an amount of MelB proteins extracted at 0° C.;
19(b) a histogram in which an amount of MelB proteins extracted at 0° C. is expressed by a percentage (%) of the total protein amount existing in a membrane sample (Memb) that is not treated with amphiphiles; and
19(c) SDS-PAGE and Western Blotting results showing an amount of MelB proteins extracted at four different temperatures of 0, 45, 55 and 65° C.
Figure 19A:
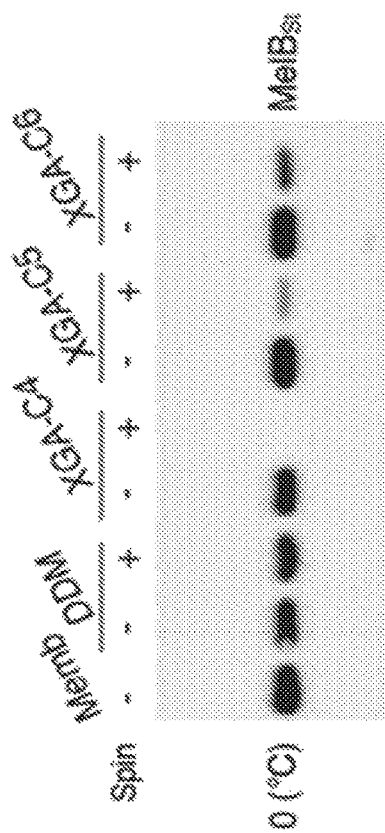
Figure 19C:
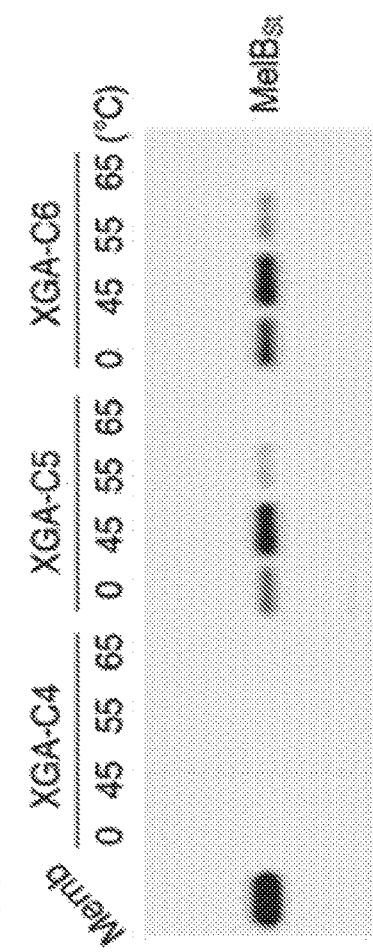

A result of measuring the thermal stability of MelB$_{St}$ dissolved in XGAs (XGA-C4, XGA-C4 and XGA-C5) which are the dialkylated versions of MGAs is shown in FIG. 19 for comparison. That is, the same experiment was conducted except that XGAs were used instead of MGAs in the experiment. As a result, the ability of MelB$_{St}$ extraction from membranes at 0° C. and the ability of MelB$_{St}$ stabilization at a high temperature of all XGAs were lower than those of DDM. These results show that a trialkylated MGA is more excellent in ability of preserving the solubility and stability of MelB$_{St}$ than a dialkylated XGA.

It can be seen from these results that MGAs of the present invention have a greater MelB protein stabilization ability than DDM and higher MelB$_{St}$ extraction efficiency than DDM at 45° C. and 55° C. Furthermore, it can be determined that MGAs with three hydrophobic groups (alkyl chains) of the present invention have greater MelB$_{St}$ solubilization and stabilization abilities than XGAs with two hydrophobic groups (alkyl chains).

<Experimental Example 4> Evaluation of LeuT Membrane Protein Structure Stabilization Ability of MGAs An experiment for measuring the structural stability of LeuT proteins according to MGAs (MGA-C11, MGA-C12, MGA-C13, MGA-C14 and MGA-C15) was performed. Each amphiphile was used at a concentration of (a) CMC+0.04 wt % or (b) CMC+0.2 wt %, a ligand-binding activity of LeuT was measured by scintillation proximity assay (SPA) using [$^3$H]-Leucine. The measurement was performed at regular intervals at room temperature during 12 days of incubation.

Specifically, a thermophilic bacteria *Aquifex aeolicus*-derived wild type LeuT was purified using a previously described method (*Nature*, G. Deckert et al., 1998, 392, 353-358). To sum up, the LeuT was expressed in *E. coli* C41 (DE3) cultured in a lysogeny broth medium supplemented with 0.1 mg/ml ampicillin. Expression of proteins was induced by adding isopropyl β-D-thiogalactopyranoside to a final concentration of 0.1 mM.

A cell membrane was separated from a crushed cell (Constant Systems Homogenizers, Kennesaw, Ga.), and solubilized in 1% (w/v) n-dodecyl-β-D-maltopyranoside (DDM; Affymetrix, Santa Clara, Calif.). After solubilization, LeuT was fixed in a Ni$^2$+-NTA resin (Life Technologies, Denmark), and eluted in 20 mM Tris-HCl (pH 7.5), 199 mM KCl, 1 mM NaCl, 0.05% (w/v) DDM and 300 mM imidazole. Thereafter, purified LeuT (about 1.5 mg/ml) was diluted tenfold with a buffer supplemented with MGA (MGA-C11, MGA-C12, MGA-C13, MGA-C14 or MGA-C15) or DDM to the final concentration of CMC+0.04% (w/v) or CMC+0.2% (w/v) while excluding DDM and imidazole from the above-described buffers. Protein samples were stored at room temperature for 12 days, and protein activity was determined by measuring [$^3$H]-Leu binding by SPA at a specified time. SPA was carried out using 450 mM NaCl and buffers containing each MGA, and a SPA reaction was performed in the presence of 20 nM [$^3$H]-Leu and 1.25 mg/ml copper chelate (His-Tag) YSi beads (Perkin Elmer, Denmark). [$^3$H]-Leu binding was measured using a Micro-Beta liquid scintillation counter (Perkin Elmer).

Figures 20A, 20B:
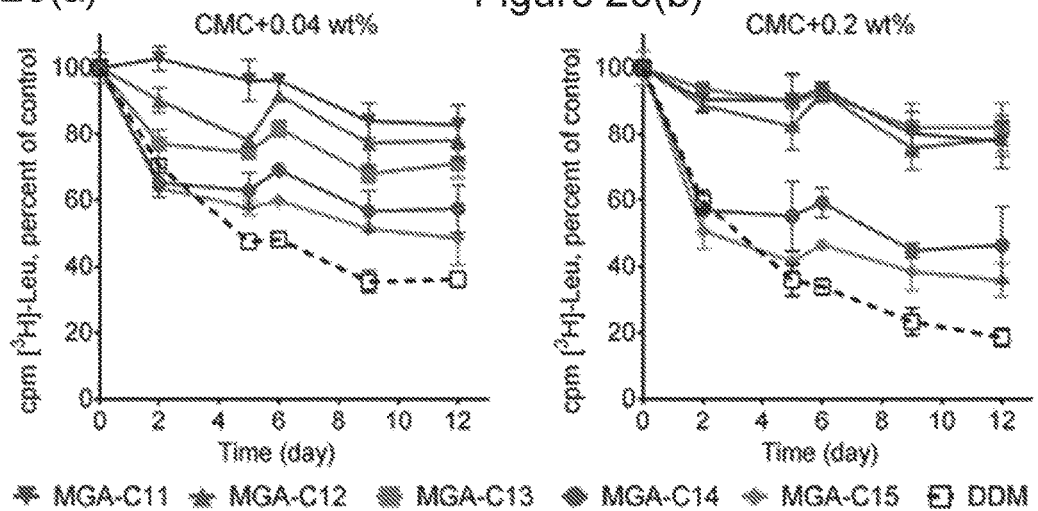
FIGS. 20(a) and 20(b) illustrate a result of measuring the structural stability of leucine transporter (LeuT) solubilized in MGAs (MGA-C 11, MGA-C12, MGA-C13, MGA-C14 and MGA-C15) or DDM in an aqueous solution. Protein stability was determined by measuring ligand-binding activity of receptors using scintillation proximity assay (SPA). The ligand-binding activity of the transporter was measured at regular intervals while LeuT was incubated at room temperature for 12 days in the presence of each amphiphile.

As illustrated in FIG. 20, LeuT solubilized by DDM gradually lost ligand-binding activity over time, and just maintained ~40% of the initial activity after 12 days of incubation. In contrast to this, all MGAs were more excellent in preservation of the long-term stability of LeuT than DDM, and specifically, MGA-C11 was the most excellent MGA, followed by MGA-C12 and MGA-C13. LeuT solubilized by MGA-C11 retained ligand-binding activity (~90%) after 12-day of incubation.

Further, results of performing the same experiment on XGAs (XGA-C4, XGA-C5 and XGA-C6) which are dialkylated compounds are shown in FIG. 21. As a result, XGAs showed a lower LeuT protein stability preservation effect than DDM.

Accordingly, it was determined that MGAs were excellent in LeuT stabilization because MGAs showed improved efficiency of preserving the ligand binding activity of LeuT as compared to DDM or XGAs.

<Experimental Example 5> Evaluation of β$_2$AR Membrane Protein Structure Stabilization Ability of MGAs An experiment for measuring the structural stability of human β$_2$-adrenergic receptor (β$_2$AR), a G-protein-linked receptor (GPCR), solubilized in MGAs was carried out.

<5-1> Measurement of Ligand (DHA) Binding Activity of β$_2$AR Using Radioligand Binding Experiment The activity of a receptor (β$_2$AR) purified by DDM or MGAs (MGA-C12, MGA-C13 and MGA-C14) was measured by binding of [$^3$H]-dihydroalprenolol ([$^3$H]-DHA).

Specifically, the following method was used in a radioligand binding experiment. β$_2$AR was purified by 0.1% DDM. The DDM-purified β$_2$AR was diluted with a buffer solution containing each amphiphile (DDM or an MGA) such that the final concentration of the amphiphile was CMC+0.2 wt %. β$_2$AR dissolved in each amphiphile was stored at room temperature for three days, and incubated at room temperature for 30 minutes using 10 nM-radioactive [$^3$H]-dihydroalprenolol (DHA) to measure ligand binding thereof at regular intervals. The mixture was loaded into a G-50 column, and passing liquid was collected using a binding buffer (20 mM HEPES pH 7.5, 100 mM NaCl supplemented with 0.5 mg/ml BSA) and 15 ml of a scintillation fluid was added thereto. Receptor-coupled [$^3$H]-DHA was measured by a scintillation counter (Beckman). Non-specific binding of [$^3$H]-DHA was measured by adding 1 μM of alprenolol (Sigma) in the same reaction. Binding of [$^3$H]-DHA was measured by column graphs.

As illustrated in FIG. 22, the initial receptor activity of MGAs (MGA-C12, MGA-C13 or MGA-C14) was similar to that of DDM.

However, as illustrated in FIG. 23, as a result of monitoring receptor stability at regular intervals for three days of incubation at room temperature, a difference between MGAs and DDM was observed. Receptors solubilized by DDM rapidly lost activity over time to retain only ~15% of receptor activity after three days of incubation. However, receptors solubilized by MGA-C13 or MGA-C14 slowly lost ligand binding activity of the receptor, and maintained enhanced activity of 50-60% after 3-day of incubation.

<5-2> Size Exclusion Chromatography (SEC) Experiment

A size exclusion chromatography (SEC) experiment was conducted to determine the β$_2$AR crystallization effect and β$_2$AR stability preservation effect by MGA-C13 or DDM.

Specifically, β$_2$AR purified by 0.1% DDM was mixed with a DDM or MGA-C13 buffer (20 mM HEPES pH 7.5, 100 mM NaCl, 0.2% of each amphiphile) and incubated for 30 minutes. The sample was applied to a Superdex-200 10/300 GL column (GE Healthcare Life Sciences) at a rate of 0.5 ml/min, fluorescence was recorded at 345 nm, and an emission wavelength was 295 nm. A running buffer contained 20 mM HEPES (pH 7.5) and 100 mM NaCl, and contained each amphiphile (DDM or MGA-C13) or not.

As illustrated in FIG. 24a, MGA-C13 formed smaller protein-detergent complexes (PDCs) than DDM. This indicates that MGA-C13 has an excellent membrane protein crystallization effect.

As illustrated in FIG. 24b, as a result of applying β$_2$AR solubilized with DDM or MGA-C13 to a SEC column in an amphiphile-free buffer environment, the receptor solubilized with DDM showed a largely decreased monodispersed peak intensity (~13 mL) and a new broad aggregate peak (~10 mL). In contrast to this, the receptor solubilized with MGA-C13 had almost no change under these conditions. Thus, it was determined that MGA-C13 was capable of preserving the stability of the receptor even in an amphiphile-free buffer, and this was because MGA-C13 formed a strong interaction with the receptor.

<Comparative Example 2> Comparison of MGAs and MNG-3

An experiment for comparison of maltose-neopentyl glycol-3 (MNG-3; see *Protein Cell*, He, Y. et al., 2014, 5, 658.

and *Structure*, Hauer, F. et al., 2015, 23, 1769.) which is known to have an excellent performance as a novel amphiphile for membrane protein research and MGAs (MGA-C13, MGA-C14) was conducted.

Specifically, a UapA stabilization effect was evaluated by the same method as in Experimental Example 2 using MGA-C13, MGA-C14, MNG-3 or DDM at a concentration of (a) CMC+0.04 wt % or (b) CMC+0.2 wt %.

As illustrated in FIG. 25, it was determined that MGA-C13 and MGA-C14 had a far greater UapA stabilization effect than MNG-3.

When a mesitylene-cored compound according to an embodiment of the present invention is used, membrane proteins can be stored in a stable conformation for a long time in an aqueous solution in comparison with conventional compounds, by which the membrane proteins are usable in both functional and structural analyses thereof.

The functional and structural analyses of membrane proteins are one of the fields that are most spotlighted in current biology and chemistry, and thus are applicable to research on a protein structure closely related to new drug development.

Specifically, a compound according to an embodiment of the present invention allows protein-detergent complexes (PDCs) with a small size with a membrane protein such that membrane protein crystals with high quality can be obtained, and has a mesitylene linker that is structurally rigid. Moreover, since the flexibility of a whole molecule is highly restricted by introducing three quaternary carbons to terminal ends of mesitylene, crystallization of a membrane protein can be promoted.

Furthermore, since a compound according to an embodiment of the present invention can be synthesized from readily available starting materials using a simple synthetic method, mass production of the compound for membrane protein research can be realized.

The above description for the present invention is merely for an example, and it will be apparent to those skilled in the art that various modifications can be made to the above-described exemplary embodiments of the present invention without departing from the spirit or scope of the invention.

Thus, it is intended that the above-described embodiments of the present invention are merely exemplified in all aspects and the present invention is not limited thereto.

What is claimed is:

1. A compound represented by the following Formula 1:

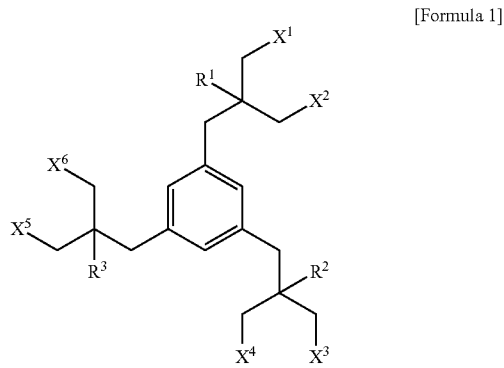

[Formula 1]

wherein in Formula 1, $R^1$, $R^2$ and $R^3$ each independently represent a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and $X^1$, $X^2$, $X^3$, $X^4$, $X^5$ and $X^6$ each independently represent an oxygen-linked saccharide.

2. The compound according to claim 1, wherein the saccharide is a monosaccharide or a disaccharide.

3. The compound according to claim 1, wherein the saccharide is glucose or maltose.

4. The compound according to claim 1, wherein $R^1$ to $R^3$ represent a substituted or unsubstituted $C_3$ to $C_{30}$ alkyl group; and $X^1$ to $X^6$ represent an oxygen-linked glucose.

5. The compound according to claim 1, wherein the compound is a compound represented by one of the following Formulas 2 to 7:

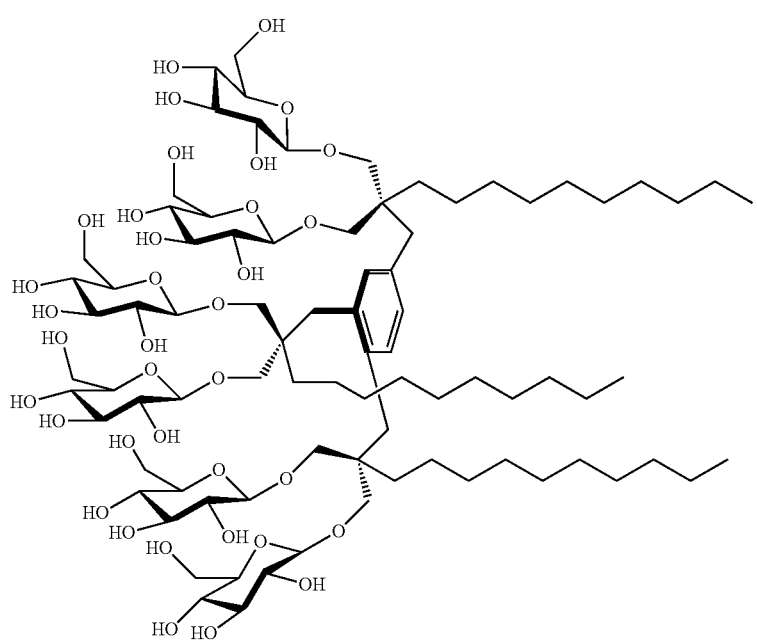

[Formula 2]

-continued
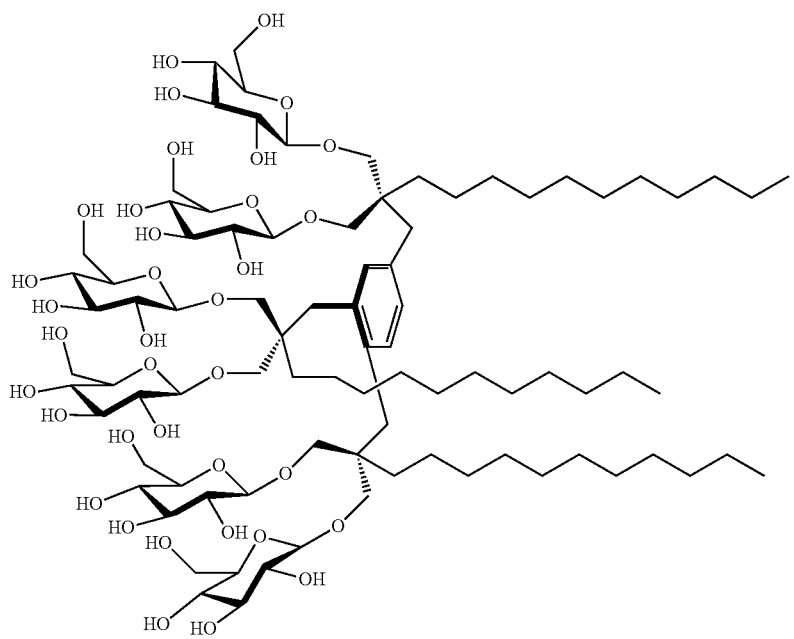
[Formula 3]
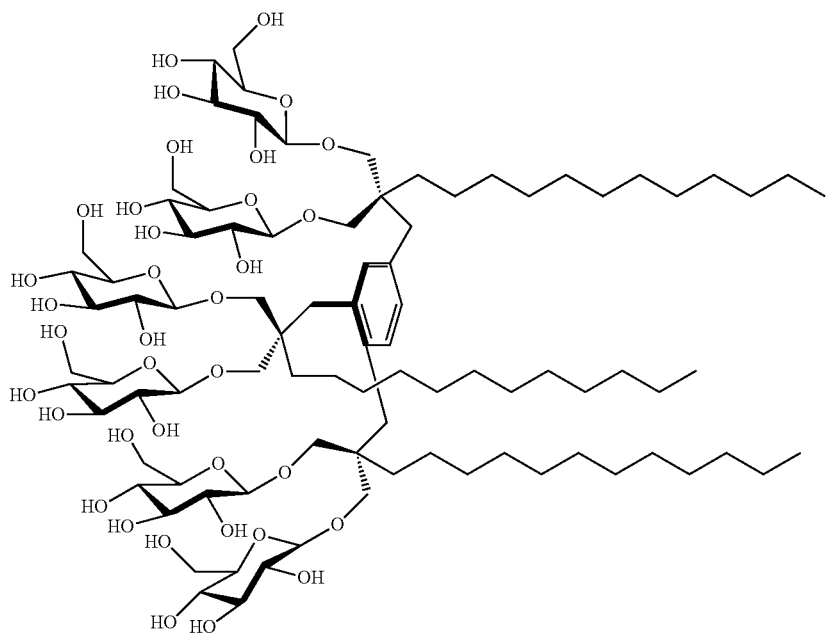
[Formula 4]

[Formula 5]
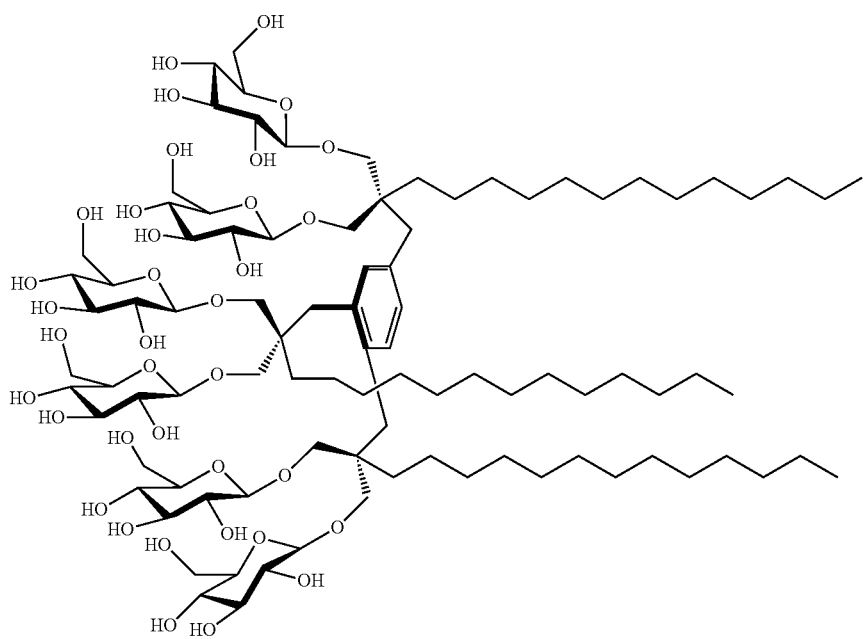
[Formula 6]
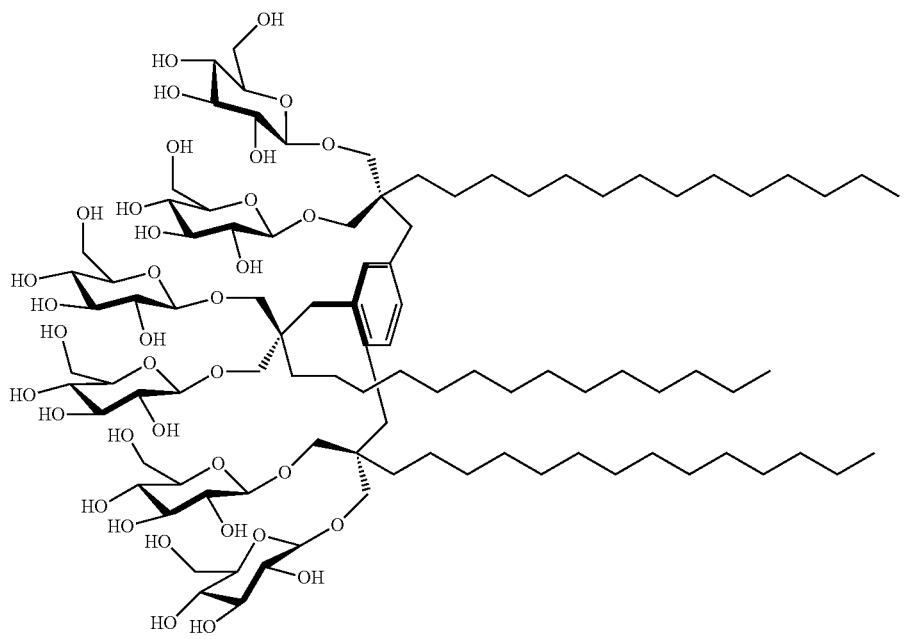

-continued

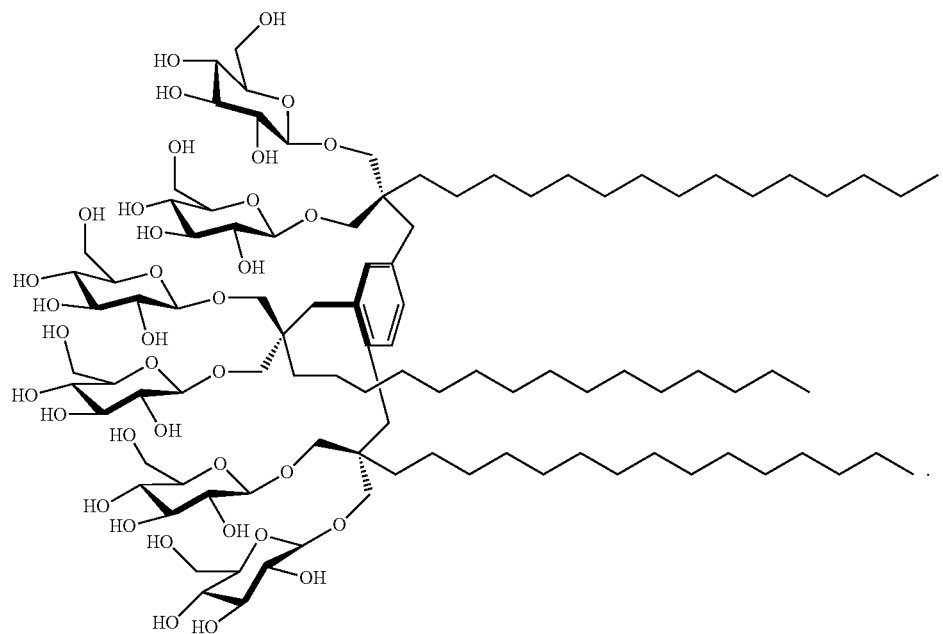

6. The compound according to claim 1, wherein the compound is an amphiphilic molecule for extraction, solubilization, stabilization, crystallization or analysis of a membrane protein.

7. The compound according to claim 1, wherein the compound has a critical micelle concentration (CMC) in a range of 0.1 to 10,000 μM in an aqueous solution.

8. A composition for extraction, solubilization, stabilization, crystallization or analysis of a membrane protein, comprising the compound according to claim 1.

9. The composition according to claim 8, wherein the composition is in a micelle, liposome, emulsion or nanoparticle form.

10. A method of preparing a compound represented by the following Formula 1, comprising the steps of:

1) performing a monoalkylation reaction on diethyl malonate to introduce an alkyl group;

2) reacting the product prepared in step 1) with 1,3,5-tris (bromomethyl)benzene to introduce a mesitylene linker;

3) reducing an ester group of the product prepared in step 2) to an alcohol group;

4) performing a glycosylation reaction on the product prepared in step 3) to introduce a saccharide with a protecting group; and 5) performing a deprotection reaction on the product prepared in step 4):

[Formula 1]

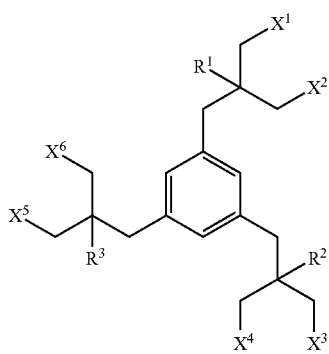

wherein in Formula 1, $R^1$, $R^2$ and $R^3$ each independently represent a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and $X^1$, $X^2$, $X^3$, $X^4$, $X^5$ and $X^6$ each independently represent an oxygen-linked saccharide.

11. The method according to claim 10, wherein $R^1$ to $R^3$ represent a substituted or unsubstituted $C_3$ to $C_{30}$ alkyl group; and $X^1$ to $X^6$ represent an oxygen-linked glucose.

12. A method of extraction, solubilization, stabilization, crystallization or analysis of a membrane protein, comprising treating a membrane protein with a compound represented by the following Formula 1 in an aqueous solution:

[Formula 1]

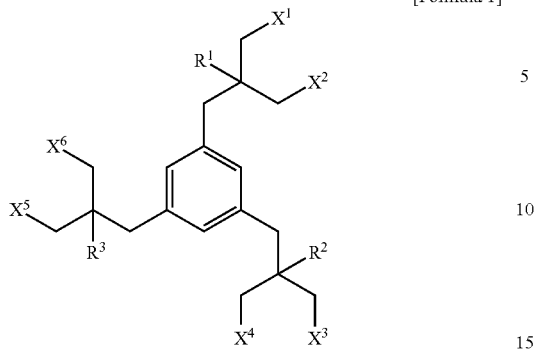

wherein in Formula 1, $R^1$, $R^2$ and $R^3$ each independently represent a substituted or unsubstituted $C_3$ to $C_{30}$ alkyl group, a substituted or unsubstituted $C_3$ to $C_{30}$ cycloalkyl group, or a substituted or unsubstituted $C_3$ to $C_{30}$ aryl group; and $X^1$, $X^2$, $X^3$, $X^4$, $X^5$ and $X^6$ each independently represent an oxygen-linked saccharide.

13. The method according to claim 12, wherein $R^1$ to $R^3$ represent a substituted or unsubstituted $C_3$ to $C_{30}$ alkyl group; and $X^1$ to $X^6$ represent an oxygen-linked glucose.

14. The method according to claim 12, wherein the membrane protein is selected from a group comprising of uric acid-xanthine/$H^+$ symporter (UapA), melibiose permease (MelB), leucine transporter (LeuT), human $\beta_2$ adrenergic receptor ($\beta_2$AR), and combinations thereof.

* * * * *